United States Patent [19]
Morris et al.

[11] Patent Number: 5,529,925
[45] Date of Patent: Jun. 25, 1996

[54] NUCLEIC ACID SEQUENCES AND FUSION PROTEINS PRESENT IN HUMAN T(2;5) LYMPHOMA

[75] Inventors: Stephan W. Morris; A. Thomas Look, both of Memphis, Tenn.

[73] Assignee: St. Jude Children's Research Hospital, Memphis, Tenn.

[21] Appl. No.: 160,861

[22] Filed: Dec. 3, 1993

[51] Int. Cl.$^6$ .............................. C12N 15/54; C12N 9/12
[52] U.S. Cl. ..................................... 435/252.3; 435/320.1; 435/194; 536/23.2
[58] Field of Search .................................. 435/194, 320.1, 435/252.3; 800/2; 536/23.2, 23.4, 23.5; 530/350, 352, 358

[56] References Cited

PUBLICATIONS

Basler, K. et al., Control of Photoreceptor Cell Fate by the sevenless Protein Requires a Functional Tyrosine Kinase Domain, *Cell* 54:299–311 (Jul. 29, 1988).

Beckmann, R. et al., Nuclear Substrates of Protein Kinase C, *Eur. J. Biochem.* 210:45–51 (1992).

Bitter, M. A. et al., Morphology in Ki–1 (CD30)–Positive Non–Hodgkin's Lymphoma Is Correlated with Clinical Features and the Presence of a Unique Chromosomal Abnormality, t(2;5)(p23;q35), *Amer. J. Surg. Pathol.* 14(4):305–316 (1990).

Borer, R. A. et al., Major Nucleolar Proteins Shuttle between Nucleus and Cytoplasm, *Cell* 56:379–390 (Feb. 10, 1989).

Bowtell, D. D. L. et al., Nucleotide sequence and structure of the sevenless gene of Drosophila melanogaster, *Genes and Development* 2:620–634 (1988).

Brinkman, A. et al., Isolation and characterization of a cDNA encoding the low molecular weight insulin–like growth factor binding protein (IBP–1), *EMBO J.* 7(8):2417–2423 (1988).

Chan, P. K. et al., The major phosphorylation site of nucleophosmin (B23) is phosphorylated by a nuclear kinase II, *Biochem. J.* 270:549–552 (1990).

Chan, W. et al., Characterization of the cDNA Encoding Human Nucleophosmin and Studies of Its Role in Normal and Abnormal Growth, *Biochemistry* 28(3):1033–1039 (1989).

Chen, J. et al., The proto–oncogene c–ros codes for a transmembrane tyrosine protein kinase sharing sequence and structural homology with sevenless protein of Drosophila melanogaster, *Oncogene* 6:257–264 (1991).

Cleary, M. L., Oncogenic Conversion of Transcription Factors by Chromosomal Translocations, *Cell* 66:619–622 (Aug. 23, 1991).

Coulier, F. et al., Mechanism of Activation of the Human trk Oncogene, *Mol. Cell. Biol* 9(1):15–23 (Jan. 1989).

Dumbar, T. S. et al., Interaction of Nucleolar Phosphoprotein B23 with Nucleic Acids, *Biochemistry* 28(24):9495–9501 (1989).

Dürkop, H. et al., Molecular Cloning and Expression of a New Member of the Nerve Growth Factor Receptor Family That Is Characteristic for Hodgkin's Disease, *Cell* 68:421–427 (Feb. 7, 1992).

Ebina, Y. et al., The Human Insulin Receptors cDNA: The Structural Basis for Hormone–Activated Transmembrane Signalling, *Cell* 40:747–758 (Apr. 1985).

Feuerstein, N. et al., "Numatrin," a Nuclear Matrix Protein Associated with Induction of Proliferation in B Lymphocytes, *J. Biol. Chem.* 262(23):11389–11397 (Aug. 15, 1987).

Feuerstein, N. et al., Identification of Numatrin, the Nuclear Matrix Protein Associated with Induction of Mitogenesis, as the Nuclear Protein B23, *J. Biol. Chem.* 263(22):10608–10612 (Aug. 5, 1988).

Feuerstein, N. et al., In Vivo and in Vitro Phosphorylation Studies of Numatrin, a Cell Cycle Regulated Nuclear Protein, in Insulin–Stimulated NIH 3T3 HIR Cells, *Exper. Cell Res.* 194:289–296 (1991).

Feuerstein, N. et al., Identification Of A Prominent Nuclear Protein Associated With Proliferation Of Normal And Malignant B Cells, *J. Immunol.* 139(6):1818–1822 (Sep. 15, 1987).

Feuerstein, N. et al., The Nuclear Matrix Protein, Numatrin (B23), Is Associated with Growth Factor–induced Mitogenesis in Swiss 3T3 Fibroblasts and with T Lymphocyte Proliferation Stimulated by Lectins and Anti–T Cell Antigen Receptor Antibody, *J. Cell Biol.* 107:1629–1642 (Nov. 1988).

Greer, J. P. et al. Clinical Features of 31 Patients With Ki–1 anaplastic Large–Cell Lymphoma, *J. Clin. Oncol.* 9(4):539–547 (Apr. 1991).

Hanks, S. K. et al., The Protein Kinase Family: Conserved Features and Deduced Phylogeny of the Catalytic Domains, *Science* 241:42–52 (Jul. 1, 1988).

Hernandez–Verdun, D., The nucleolus today, *J. Cell Sci.* 99:465–471 (1991).

Julkunen, M. et al., Primary structure of human insulin–like growth factor–binding protein/placental protein 12 and tissue–specific expression of its mRNA, *FEBS Letters* 236(2):295–302 (Aug. 1988).

Kadin, M. E., Ki–1–Positive Anaplastic Large–Cell Lymphoma: A Clinicopathologic Entity?, *J. Clin. Oncol.* 9(4):533–536 (Apr. 1991).

Kaneko, Y. et al., A Novel Translocation, t(2;5)(p23;q35), in Childhood Phagocytic Large T–Cell Lymphoma Mimicking Malignant Histiocytosis, *Blood* 73(3):806–813 (Feb. 15, 1989).

Kozma, S. C. et al., Activation of the receptor kinase domain (List continued on next page.)

*Primary Examiner*—Charles L. Patterson, Jr.
*Assistant Examiner*—Keith D. Hendricks
*Attorney, Agent, or Firm*—Sterne, Kessler, Goldstein & Fox

[57] ABSTRACT

The present invention is based on the identification and sequence determination of fusion proteins generated by translocation which is present in t(2;5) lymphoma cells. Using either the amino acid or nucleic acid sequences of the fusion proteins disclosed herein, the present invention provides methods of detecting and treating t(2;5) lymphoma.

5 Claims, 8 Drawing Sheets

OTHER PUBLICATIONS of the trk oncogene by recombination with two different cellular sequences, *EMBO J.* 7(1):147–154 (1988).

Krolewski, J. J. et al., The ltk gene encodes a novel receptor-type protein tyrosine kinase, *EMBO J.* 10(10):2911–2919 (1991).

Lawrence, J. B. et al., Interphase and Metaphase Resolution of Different Distances Within the Human Dystrophin Gene, *Science* 249:928–932 (Aug. 24, 1990).

Le Beau, M. M. et al., The t(2;5)(p23;q35): A Recurring Chromosomal Abnormality in K–1–Positive Anaplastic Large Cell Lymphoma, *Leukemia 3(12):866–870 (Dec. 1989).*

Lee, Y. et al., Insulin–Like Growth Factor (IGF) Binding Protein Complementary Deoxyribonucleic Acid from Human HEP G2 Hepatoma Cells: Predicted Protein Sequence Suggests an IGF Binding Domain Different from Those of the IGF–I and IGF–II Receptors, *Mol. Endocrinol.* 2(5):404–411 (1988).

Martin–Zanca, D. et al., A human oncogene formed by the fusion of truncated tropomysin and protein tyrosine kinase sequences, *Nature* 319:743–748 (Feb. 27, 1986).

Mason, D. Y. et al., CD30–positive large cell lymphomas ('Ki–1 lymphoma') are associated with a chromosomal translocation involving 5q35, *Br. J. Hematol.* 74:161–168 (1990).

Matsushime, H. et al., Human c–ros–1 Gene Homologous to the v–ros Sequence of UR2 Sarcoma Virus Encodes for a Transmembrane Receptorlike Molecule, *Mol. Cell. Biol.* 6(8):3000–3004 (Aug. 1986).

Morris, S. W. et al., Reassignment of the Human CSF1 Gene to Chromosome 1p13–p21, *Blood* 78(8):2013–2020 (Oct. 15, 1991).

Oskam, R. et al., Frequent generation of oncogenes by in vitro recombination of TRK protooncogene sequences, *Proc. Natl. Acad. Sci. USA* 85:2964–2968 (May 1988).

Pawson, T., Tyrosine kinases and their interactions with signalling proteins, *Curr. Opin. Genet. Devel.* 2:4–12 (1992).

Peter, M. et al., Identification of Major Nucleolar Proteins As Candidate Mitotic Substrates of cdc2 Kinase, *Cell* 60:791–801 (Mar. 9, 1990).

Rabbitts, T. H., Translocations, Master Genes, and Differences between the Origins of Acute and Chronic Leukemias, *Cell* 67:641–644 (Nov. 15, 1991).

Rimokh, R. et al., A translocation involving a specific breakpoint (q35) on chromosome 5 is characteristic of anaplastic large cell lymphoma ('Ki–1 lymphoma'), *Br. J. Hematol.* 71:31–36 (1989).

Saltman, D. L. et al., A Physical Map of 15 Loci on Human Chromosome 5q23–q33 by Two–Color Fluorescence in Situ Hybridization, *Genomics* 16:726–732 (1993).

Saltman, D. L. et al., Isolation of region–specific cosmids from chromosome 5 by hybridization with microdissection clones, *Nucleic Acids Research* 20(6):1401–1404 (1992).

Sawyers, C. L. et al., Leukemia and the Disruption of Normal Hematopoiesis, *Cell* 64:337–350 (Jan. 25, 1991).

Schlessinger, J. et al., Growth Factor Signaling by Receptor Tyrosine Kinases, *Neuron* 9:383–391 (Sep. 1992).

Schmidt–Zachmann, M. S. et al., A constitutive nucleolar protein identified as a member of the nucleoplasmin family, *EMBO J.* 6(7):1881–1890 (1987).

Schmidt–Zachmann, M. S. et al., DNA cloning and amino acid sequence determination of a major constituent protein of mammalian nucleoli, *Chromosoma* (Berl) 96:417–426 (1988).

Selleri, L. et al., Molecular localization of the t(11;22)(q24;q12) translocation of Ewing sarcoma by chromosomal in situ suppression hybridization, *Proc. Natl. Acad. Sci. USA* 88:887–891 (Feb. 1991).

Smith, C. A. et al., CD30 Antigen, a Marker for Hodgkin's Lymphoma, Is a Receptor Whose Ligand Defines an Emerging Family of Cytokines with Homology to TNF, *Cell* 73:1349–1360 (Jul. 2, 1993).

Smith, K. A., Interleukin–2: Inception, Impact, and Implications, *Science* 240:1169–1176 (May 27, 1988).

Stansfeld, A. G. et al., Updated Kiel Classification For Lymphomas, *The Lancet* 1:292–293 (Feb. 6, 1988).

Stein, H. et al., Diffuse Large Cell Lymphomas of B and T Cell Type, in Knowles, D. M., ed., *Neoplastic Hematopathology*, Williams & Wilkins, Baltimore, pp. 675–714 (1992).

Taylor, S. S. et al., Structural Framework For The Protein Kinase Family, *Annu. Rev. Cell Biol.* 8:429–462 (1992).

Tkachuk, D. C. et al., Detection of bcr–abl Fusion in Chronic Myelogeneous Leukemia by in Situ Hybridization, *Science* 250:559–562 (Oct. 26, 1990).

Toyoshima, H. et al., Differently spliced cDNAs of human leukocyte tyrosine kinase receptor tyrosine kinase predict receptor proteins with and without a tyrosine kinase domain and a soluble receptor protein, *Proc. Natl. Acad. Sci. USA* 90:5404–5408 (Jun. 1993).

Trask, B. J. et al., Mapping of Human Chromosome Xq28 by Two–Color Fluorescence In Situ Hybridization of DNA Sequences to Interphase Cell Nuclei, *Am. J. Hum. Genet.* 48:1–15 (1991).

Ullrich, A. et al., Human insulin receptor and its relationship to the tyrosine kinase family of oncogenes, *Nature* 313:756–761 (Feb. 28, 1985).

Ullrich, A. et al., Insulin–like growth factor I receptor primary structure: comparison with insulin receptor suggests structural determinants that define functional specificity, *EMBO J.* 5:2503–2512 (1986).

Vecchi, V. et al., Anaplastic Large Cell Lymphoma (Ki–1+/CD30+) in Childhood, *Med. Pediatr. Oncol.* 21:402–410 (1993).

Ziemiecki, A. et al., Oncogenic activation of the human trk proto–oncogene by recombination with the ribosomal large subunit protein L7a, *EMBO J.* 9(1):191–196 (1990).

MEDSMDMDMSPLRPQNYLFGCELKADKDYHFKVDNDENEHQL·SLRTVSLGAGAKDELHIVEAEAMNYEGSPIKVTLATLK  80

MSVQPTVSLGGFEITPPVVLRLKCGSGPVHISGQHLVVYRRKHQELQAMQMELQSPEYKLSKLRTSTIMTDYNPNYCFAG  160
                                  ←—NPM | ALK—→

KTSSISDLKEVPRKNITLIRGLGHGAFGEVYEGQVSGMPNDPSPLQVAVKTLPEVCSEQDELDFLMEALIISKFNHQNIV  240
              ↓ * *                                    *

RCIGVSLQSLPRFILLELMAGGDLKSFLRETRPRPSQPSSLAMLDLLHVARDIACGCQYLEENHFIHRDIAARNCLLTCP  320

GPGRVAKIGDFGMARDIYRASYYRKGGCAMLPVKWMPPEAFMEGIFTSKTDTWSFGVLLWEIFSLGYMPYPSKSNQEVLE  400
                              ↓

VTSGGRMDPPKNCPGPVYRIMTQCWQHQPEDRPNFAIILERIEYCTQDPDVINTALPIEYGPLVEEEKVPVRPKDPEGV  480

PPLLVSQQAKREEEQPSCPTTSAYHLLWQGCKETHSCRGLCSSP  525

FIG.2A

VNIKHYLNCSHCEVDECHMDPESHKVICFCDHGTVLAEDGVSCIVSPTPEPHLP|SLILSVVTSALVAALVLAFSGIM|VYRRKHQELQAMQMELQSPEY
                                                                           ↓

FIG.2B

```
         LGHGAFGEVYEGQVSGMPNDPS-PLQVAVKTLPEVCSEQDELDFLMEALIISKFNHQNIVRCIGVSLQSLPRFILLE
ALK      LGHGAFGEVYEGVVLVIGLPGDSS-PLQVAIKTLPELGSPQDELDFLMEALIISKFRHQNIVRCVGLSLRATPRLILLE
LTK      LGEGAFGKVFLAECHNLLPEQD-KMLVAVKALKE-ASESARQFQREAELTMLQHQHIVRFFGVCTEGRPLLMVFE
TRKA     LGSGAFGEVYEGTAVDILGVGSGEIKVAVKTLKKGSTDQEKIEFLKEAHLMSKFNHPNILKQLGVCLLNEPQYIILE
ROS      LGSGAFGEVYEGQLQA--EDEAQPQRVAIKSLRKGAS--EFAELLQEAQLMSNFKHENIVCLIGICCDTDSISLIME
7les     LGQGSFGMVYEGVAKGVVKDEP-ETRVAIKTVNEAASMRERIEFLNEASVMKEFNCHHVRLLGVVSGQPTLVIME
IGF1R    LGQGSFGMVYEGNARDIIKGEA-ETRVAVKTVNESASLRERIEFLNEASVMKGFTCHHVRLLGVVSKGQPTLVVME
IR LMAGGDLKSFLRETRPRP-------SQPSSLAMLDLLHVARDIACGCQYLEENHFIHRDIAARNCLLTCP----GPG
ALK      LMSGGDMKSFLRHSRPHL-------GQPSPLVMRDLLQLAQDIAQGCHYLEENHFIHRDIAARNCLLSCA----GPS
LTK      YMRHGDLNRFLRSHGPDAKLLAGGEDVAPGPLGLGQLLAVASQVAAGMVYLAGLHFVHRDLATRNCLV-----GQG
TRKA     LMEGGDLLTYLRKARMATFY-----G-PLLTLVDLVDLCVDISKGCYLEDMHFVHRDLACRNCLVS-VKDYTSP
ROS      HMEAGDLLSYLRAARPSSQE------ALSKLQLPELLSMCLDVANGCSYEDMHFVHRDLAARNCMV-----AED
7les     LMTRGGDLKSYLRSLRPEM-------ENNPVLAPPSLSKMIQMAGEIADGMAYLNANKFVHRDLAARNCMV-----AHD
IGF1R    LMAHGDLKSYLRSLRPEA-------ENNPGRPPPTLQEMIQMAAEIADGMAYLNAKKFVHRDLAARNCMV-----AHD
IR RVAKIGDFGMARDIYRASYYRKGGCAMLPVKWMPPEAFMEGIFTSKTDTWSFGVLLWEIFSLGYMPYPSKSNQEVLE
ALK      RVAKIGDFGMARDIYRASYYRKGGCAMLPVKWMPPEAFLEGIFTSKTDTWSFGVLLWEIFSLGYMPYPGRTNQEVLD
LTK      LVVKIGDFGMSRDIYSTDYYRVGGRTMLPIRWMPPESILYRKFTTESDVWSFGVLLWEIFTYGKQPWYQLSNTEAID
TRKA     RIVKIGDFGLARDIYKNDYYRKRGEGLLPVRWMAPESLKDGIFITQSDVWSFGILIWEILTLGHQPYPAHSNLDVLN
ROS      RIVKIGDFGLARDIYKSDYYRKEGEGLLPVRWMALESLVDGLFSTQSDVWSFGVAFGVLCWEIFTLGQQPYAARNFEVLA
7les     FTVKIGDFGMTRDIYETDYYRKGGKGLLPVRWMSPESLKDGVFTTYSDVWSFGVVLWEIATLAEQPYQGLSNEQVLR
IGF1R    FTVKIGDFGMTRDIYETDYYRKGGKGLLPVRWMAPESLKDGLLPVRWMAPESLKDGVFTTSSDMWSFGVVLWEITSLAEQPYQGLSNEQVLK
IR FVTSGGRMDPPKNCPGPVYRIMTQCWQHQPEDRPNF
ALK      FVGGGRMDPPRGCPGPVYRIMTQCWQHQPELRPSF
LTK      CITQGRELERPRACPPEVYAIMRGCWQREPQQRHSI
TRKA     YQTGGRLEPPRNCPDDLWNLMTQCWAQEPDQRPTF
ROS      HVKEGGRLQQPERCPEKLYALLLQCWRSEPWERPSF
7les     FVMEGGLLDKPDNCPDMLFELMRMCWQYNPKMRPSF
IGF1R    FVMDGGYLDQPDNCPERVTDLMRMCWQFNPKMRPTF
IR
```

FIG.2C

```
S   L   G   G   F   E   I   T   P   P   V   L   R   L   K   C   G   S   G
TCCCTTGGGGGGCTTTGAAATAACACCACCAGTGGTCTTAAGGTTGAAGTGTGGTTCAGGG

P   V   H   I   S   G   Q   H   L   V   V   Y   R   K   H   Q   E   L   Q
                                            NPM | ALK
CCAGTGCATATTAGTGGACAGCACTTAGTAGTGTACCGGAAGCACCAGGAGCTGCAA

A   M   Q   M   E   L   Q   S   P   E   Y   K   L   S   K   L   R   T   S
GCCATGCAGATGGAGCTGCAGAGCCCCTGAGTACAAGCTGAGCAAGCTCCGCACCTCG
```

FIG. 3B

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 2608 base pairs
        ( B ) TYPE: nucleic acid
        ( C ) STRANDEDNESS: both
        ( D ) TOPOLOGY: linear ( i i ) MOLECULE TYPE: DNA ( i x ) FEATURE:
        ( A ) NAME/KEY: CDS
        ( B ) LOCATION: 1..1719

( x i ) SEQUENCE DESCRIPTION: SEQ ID NO:1:

```
AAA  TCT  TTG  CAG  GAG  GGT  GCC  ACC  GGA  GGA  CAT  TCC  TGC  CCC  CAG  GCC         48
Lys  Ser  Leu  Gln  Glu  Gly  Ala  Thr  Gly  Gly  His  Ser  Cys  Pro  Gln  Ala
 1              5                        10                       15

ATG  AAG  AAG  TGG  GGG  TGG  GAG  ACA  AGA  GGG  GGT  TTC  GGA  GGG  GGT  GGA         96
Met  Lys  Lys  Trp  Gly  Trp  Glu  Thr  Arg  Gly  Gly  Phe  Gly  Gly  Gly  Gly
                 20                      25                      30

GGG  GGG  TGC  TCC  TCA  GGT  GGA  GGA  GGC  GGA  GGA  TAT  ATA  GGC  GGC  AAT        144
Gly  Gly  Cys  Ser  Ser  Gly  Gly  Gly  Gly  Gly  Gly  Tyr  Ile  Gly  Gly  Asn
           35                       40                       45

GCA  GCC  TCA  AAC  AAT  GAC  CCC  GAA  ATG  GAT  GGG  GAA  GAT  GGG  GTT  TCC        192
Ala  Ala  Ser  Asn  Asn  Asp  Pro  Glu  Met  Asp  Gly  Glu  Asp  Gly  Val  Ser
      50                      55                       60

TTC  ATC  AGT  CCA  CTG  GGC  ATC  CTG  TAC  ACC  CCA  GCT  TTA  AAA  GTG  ATG        240
Phe  Ile  Ser  Pro  Leu  Gly  Ile  Leu  Tyr  Thr  Pro  Ala  Leu  Lys  Val  Met
 65                      70                       75                      80

GAA  GGC  CAC  GGG  GAA  GTG  AAT  ATT  AAG  CAT  TAT  CTA  AAC  TGC  AGT  CAC        288
Glu  Gly  His  Gly  Glu  Val  Asn  Ile  Lys  His  Tyr  Leu  Asn  Cys  Ser  His
```

|  |  |  |  |  |  |  |  |  |  |  |  |  |  |  |  |
|---|---|---|---|---|---|---|---|---|---|---|---|---|---|---|---|
|  |  |  |  |  | 85 |  |  |  |  | 90 |  |  |  |  | 95 |

| | | | | | | | | | | | | | | | | |
|---|---|---|---|---|---|---|---|---|---|---|---|---|---|---|---|---|
| TGT | GAG | GTA | GAC | GAA | TGT | CAC | ATG | GAC | CCT | GAA | AGC | CAC | AAG | GTC | ATC | 336 |
| Cys | Glu | Val | Asp | Glu | Cys | His | Met | Asp | Pro | Glu | Ser | His | Lys | Val | Ile | |
| | | | 100 | | | | 105 | | | | | | 110 | | | |
| TGC | TTC | TGT | GAC | CAC | GGG | ACG | GTG | CTG | GCT | GAG | GAT | GGC | GTC | TCC | TGC | 384 |
| Cys | Phe | Cys | Asp | His | Gly | Thr | Val | Leu | Ala | Glu | Asp | Gly | Val | Ser | Cys | |
| | | 115 | | | | | 120 | | | | | 125 | | | | |
| ATT | GTG | TCA | CCC | ACC | CCG | GAG | CCA | CAC | CTG | CCA | CTC | TCG | CTG | ATC | CTC | 432 |
| Ile | Val | Ser | Pro | Thr | Pro | Glu | Pro | His | Leu | Pro | Leu | Ser | Leu | Ile | Leu | |
| | 130 | | | | | 135 | | | | | 140 | | | | | |
| TCT | GTG | GTG | ACC | TCT | GCC | CTC | GTG | GCC | GCC | CTG | GTC | CTG | GCT | TTC | TCC | 480 |
| Ser | Val | Val | Thr | Ser | Ala | Leu | Val | Ala | Ala | Leu | Val | Leu | Ala | Phe | Ser | |
| 145 | | | | | 150 | | | | | 155 | | | | | 160 | |
| GGC | ATC | ATG | ATT | GTG | TAC | CGC | CGG | AAG | CAC | CAG | GAG | CTG | CAA | GCC | ATG | 528 |
| Gly | Ile | Met | Ile | Val | Tyr | Arg | Arg | Lys | His | Gln | Glu | Leu | Gln | Ala | Met | |
| | | | | 165 | | | | | 170 | | | | | 175 | | |
| CAG | ATG | GAG | CTG | CAG | AGC | CCT | GAG | TAC | AAG | CTG | AGC | AAG | CTC | CGC | ACC | 576 |
| Gln | Met | Glu | Leu | Gln | Ser | Pro | Glu | Tyr | Lys | Leu | Ser | Lys | Leu | Arg | Thr | |
| | | | 180 | | | | | 185 | | | | | 190 | | | |
| TCG | ACC | ATC | ATG | ACC | GAC | TAC | AAC | CCC | AAC | TAC | TGC | TTT | GCT | GGC | AAG | 624 |
| Ser | Thr | Ile | Met | Thr | Asp | Tyr | Asn | Pro | Asn | Tyr | Cys | Phe | Ala | Gly | Lys | |
| | | 195 | | | | | 200 | | | | | 205 | | | | |
| ACC | TCC | TCC | ATC | AGT | GAC | CTG | AAG | GAG | GTG | CCG | CGG | AAA | AAC | ATC | ACC | 672 |
| Thr | Ser | Ser | Ile | Ser | Asp | Leu | Lys | Glu | Val | Pro | Arg | Lys | Asn | Ile | Thr | |
| | 210 | | | | | 215 | | | | | 220 | | | | | |
| CTC | ATT | CGG | GGT | CTG | GGC | CAT | GGC | GCC | TTT | GGG | GAG | GTG | TAT | GAA | GGC | 720 |
| Leu | Ile | Arg | Gly | Leu | Gly | His | Gly | Ala | Phe | Gly | Glu | Val | Tyr | Glu | Gly | |
| 225 | | | | | 230 | | | | | 235 | | | | | 240 | |
| CAG | GTG | TCC | GGA | ATG | CCC | AAC | GAC | CCA | AGC | CCC | CTG | CAA | GTG | GCT | GTG | 768 |
| Gln | Val | Ser | Gly | Met | Pro | Asn | Asp | Pro | Ser | Pro | Leu | Gln | Val | Ala | Val | |
| | | | | 245 | | | | | 250 | | | | | 255 | | |
| AAG | ACG | CTG | CCT | GAA | GTG | TGC | TCT | GAA | CAG | GAC | GAA | CTG | GAT | TTC | CTC | 816 |
| Lys | Thr | Leu | Pro | Glu | Val | Cys | Ser | Glu | Gln | Asp | Glu | Leu | Asp | Phe | Leu | |
| | | | 260 | | | | | 265 | | | | | 270 | | | |
| ATG | GAA | GCC | CTG | ATC | ATC | AGC | AAA | TTC | AAC | CAC | CAG | AAC | ATT | GTT | CGC | 864 |
| Met | Glu | Ala | Leu | Ile | Ile | Ser | Lys | Phe | Asn | His | Gln | Asn | Ile | Val | Arg | |
| | | 275 | | | | | 280 | | | | | 285 | | | | |
| TGC | ATT | GGG | GTG | AGC | CTG | CAA | TCC | CTG | CCC | CGG | TTC | ATC | CTG | CTG | GAG | 912 |
| Cys | Ile | Gly | Val | Ser | Leu | Gln | Ser | Leu | Pro | Arg | Phe | Ile | Leu | Leu | Glu | |
| | 290 | | | | | 295 | | | | | 300 | | | | | |
| CTC | ATG | GCG | GGG | GGA | GAC | CTC | AAG | TCC | TTC | CTC | CGA | GAG | ACC | CGC | CCT | 960 |
| Leu | Met | Ala | Gly | Gly | Asp | Leu | Lys | Ser | Phe | Leu | Arg | Glu | Thr | Arg | Pro | |
| 305 | | | | | 310 | | | | | 315 | | | | | 320 | |
| CGC | CCG | AGC | CAG | CCC | TCC | TCC | CTG | GCC | ATG | CTG | GAC | CTT | CTG | CAC | GTG | 1008 |
| Arg | Pro | Ser | Gln | Pro | Ser | Ser | Leu | Ala | Met | Leu | Asp | Leu | Leu | His | Val | |
| | | | | 325 | | | | | 330 | | | | | 335 | | |
| GCT | CGG | GAC | ATT | GCC | TGT | GGC | TGT | CAG | TAT | TTG | GAG | GAA | AAC | CAC | TTC | 1056 |
| Ala | Arg | Asp | Ile | Ala | Cys | Gly | Cys | Gln | Tyr | Leu | Glu | Glu | Asn | His | Phe | |
| | | | 340 | | | | | 345 | | | | | 350 | | | |
| ATC | CAC | CGA | GAC | ATT | GCT | GCC | AGA | AAC | TGC | CTC | TTG | ACC | TGT | CCA | GGC | 1104 |
| Ile | His | Arg | Asp | Ile | Ala | Ala | Arg | Asn | Cys | Leu | Leu | Thr | Cys | Pro | Gly | |
| | | 355 | | | | | 360 | | | | | 365 | | | | |
| CCT | GGA | AGA | GTG | GCC | AAG | ATT | GGA | GAC | TTC | GGG | ATG | GCC | CGA | GAC | ATC | 1152 |
| Pro | Gly | Arg | Val | Ala | Lys | Ile | Gly | Asp | Phe | Gly | Met | Ala | Arg | Asp | Ile | |
| | 370 | | | | | 375 | | | | | 380 | | | | | |
| TAC | AGG | GCG | AGC | TAC | TAT | AGA | AAG | GGA | GGC | TGT | GCC | ATG | CTG | CCA | GTT | 1200 |
| Tyr | Arg | Ala | Ser | Tyr | Tyr | Arg | Lys | Gly | Gly | Cys | Ala | Met | Leu | Pro | Val | |
| 385 | | | | | 390 | | | | | 395 | | | | | 400 | |
| AAG | TGG | ATG | CCC | CCA | GAG | GCC | TTC | ATG | GAA | GGA | ATA | TTC | ACT | TCT | AAA | 1248 |
| Lys | Trp | Met | Pro | Pro | Glu | Ala | Phe | Met | Glu | Gly | Ile | Phe | Thr | Ser | Lys | |

```
                                       405                              410                              415
ACA  GAC  ACA  TGG  TCC  TTT  GGA  GTG  CTG  CTA  TGG  GAA  ATC  TTT  TCT  CTT      1296
Thr  Asp  Thr  Trp  Ser  Phe  Gly  Val  Leu  Leu  Trp  Glu  Ile  Phe  Ser  Leu
               420                      425                      430

GGA  TAT  ATG  CCA  TAC  CCC  AGC  AAA  AGC  AAC  CAG  GAA  GTT  CTG  GAG  TTT      1344
Gly  Tyr  Met  Pro  Tyr  Pro  Ser  Lys  Ser  Asn  Gln  Glu  Val  Leu  Glu  Phe
          435                      440                      445

GTC  ACC  AGT  GGA  GGC  CGG  ATG  GAC  CCA  CCC  AAG  AAC  TGC  CCT  GGG  CCT      1392
Val  Thr  Ser  Gly  Gly  Arg  Met  Asp  Pro  Pro  Lys  Asn  Cys  Pro  Gly  Pro
     450                      455                      460

GTA  TAC  CGG  ATA  ATG  ACT  CAG  TGC  TGG  CAA  CAT  CAG  CCT  GAA  GAC  AGG      1440
Val  Tyr  Arg  Ile  Met  Thr  Gln  Cys  Trp  Gln  His  Gln  Pro  Glu  Asp  Arg
465                      470                      475                      480

CCC  AAC  TTT  GCC  ATC  ATT  TTG  GAG  AGG  ATT  GAA  TAC  TGC  ACC  CAG  GAC      1488
Pro  Asn  Phe  Ala  Ile  Ile  Leu  Glu  Arg  Ile  Glu  Tyr  Cys  Thr  Gln  Asp
               485                      490                      495

CCG  GAT  GTA  ATC  AAC  ACC  GCT  TTG  CCG  ATA  GAA  TAT  GGT  CCA  CTT  GTG      1536
Pro  Asp  Val  Ile  Asn  Thr  Ala  Leu  Pro  Ile  Glu  Tyr  Gly  Pro  Leu  Val
               500                      505                      510

GAA  GAG  GAA  GAG  AAA  GTG  CCT  GTG  AGG  CCC  AAG  GAC  CCT  GAG  GGG  GTT      1584
Glu  Glu  Glu  Glu  Lys  Val  Pro  Val  Arg  Pro  Lys  Asp  Pro  Glu  Gly  Val
          515                      520                      525

CCT  CCT  CTC  CTG  GTC  TCT  CAA  CAG  GCA  AAA  CGG  GAG  GAG  GAG  CAG  CCC      1632
Pro  Pro  Leu  Leu  Val  Ser  Gln  Gln  Ala  Lys  Arg  Glu  Glu  Glu  Gln  Pro
     530                      535                      540

AGC  TGC  CCC  ACC  ACC  TCT  GCC  TAC  CAC  CTC  CTC  TGG  CAA  GGC  TGC  AAA      1680
Ser  Cys  Pro  Thr  Thr  Ser  Ala  Tyr  His  Leu  Leu  Trp  Gln  Gly  Cys  Lys
545                      550                      555                      560

GAA  ACC  CAC  AGC  TGC  AGA  GGT  CTC  TGT  TCG  AGT  CCC  TAGAGGGCCG              1726
Glu  Thr  His  Ser  Cys  Arg  Gly  Leu  Cys  Ser  Ser  Pro
               565                      570

CCCGGGGAAG  CTTGCACAGG  TCCACGGATC  CAGAAACAAG  CCCACCAGCT  TGTGGAACCC      1786

AACGTACGGC  TCCTGGTTTA  CAGAGAAACC  CACCAAAAAG  AATAATCCTA  TAGCAAAGAA      1846

GGAGCCACAC  GACAGGGGTA  ACCTGGGGCT  GGAGGGAAGC  TGTACTGTCC  CACCTAACGT      1906

TGCAACTGGG  AGACTTCCGG  GGGCCTCACT  GCTCCTAGAG  CCCTCTTCGC  TGACTGCCAA      1966

TATGAAGGAG  GTACCTCTGT  TCAGGCTACG  TCACTTCCCT  TGTGGGAATG  TCAATTACGG      2026

CTACCAGCAA  CAGGGCTTGC  CCTTAGAAGC  CGCTACTGCC  CCTGGAGCTG  AGCTGGTCA       2086

TTACGAGGAT  ACCATTCTGA  AAAGCAAGAA  TAGCATGAAC  CAGCCTGGGC  CCTGAGCTCG      2146

GTAGCACACT  CACTTCTCTT  CCTTGGGATC  CCTAAGACCG  TGGAGGAGAG  AGAGGCAATG      2206

GCTCCTTCAC  AAACCAGAGA  CCAAATGTCA  CGTTTTGTTT  TGTGCCAACC  TATTTTGAAG      2266

TACCACCAAA  AAAGCTGTAT  TTTGAAAATG  CTTTAGAAAG  GTTTTGAGCA  TGGGTTCATC      2326

CTATTCTTTC  GAAAGAAGAA  AATATCATAA  AAATGAGTGA  TAAATACAAG  GCCCAGATGT      2386

GGTTGCATAA  GGTTTTTATG  CATGTTTGTT  GTATACTTCC  TTATGCTTCT  TTTAAATTGT      2446

GTGTGCTCTG  CTTCAATGTA  GTCAGAATTA  GCTGCTTCTA  TGTTTCATAG  TTGGGGTCAT      2506

AGATGTTTCC  TTGCCTTGTT  GATGTGGACA  TGAGCCATTT  GAGGGGAGAG  GGAACGGAAA      2566

TAAAGGAGTT  ATTTGTAATG  ACAAAAAAAA  AAAAAAAAA  AA                          2608
```

( 2 ) INFORMATION FOR SEQ ID NO:2:

( i ) SEQUENCE CHARACTERISTICS:
        ( A ) LENGTH: 2440 base pairs
        ( B ) TYPE: nucleic acid
        ( C ) STRANDEDNESS: both
        ( D ) TOPOLOGY: linear ( i i ) MOLECULE TYPE: DNA ( i x ) FEATURE:
    ( A ) NAME/KEY: CDS
    ( B ) LOCATION: 74..1651

( x i ) SEQUENCE DESCRIPTION: SEQ ID NO:2:

```
CGGTTGTTCT CTGGAGCAGC GTTCTTTTAT CTCCGTCCGC CTTCTCTCCT ACCTAAGTGC          60

GTGCCGCCAC CCG ATG GAA GAT TCG ATG GAC ATG GAC ATG AGC CCC CTG          109
            Met Glu Asp Ser Met Asp Met Asp Met Ser Pro Leu
             1               5                      10

AGG CCC CAG AAC TAT CTT TTC GGT TGT GAA CTA AAG GCC GAC AAA GAT          157
Arg Pro Gln Asn Tyr Leu Phe Gly Cys Glu Leu Lys Ala Asp Lys Asp
             15                  20                  25

TAT CAC TTT AAG GTG GAT AAT GAT GAA AAT GAG CAC CAG TTA TCT TTA          205
Tyr His Phe Lys Val Asp Asn Asp Glu Asn Glu His Gln Leu Ser Leu
         30                  35                  40

AGA ACG GTC AGT TTA GGG GCT GGT GCA AAG GAT GAG TTG CAC ATT GTT          253
Arg Thr Val Ser Leu Gly Ala Gly Ala Lys Asp Glu Leu His Ile Val
 45                  50                  55                  60

GAA GCA GAG GCA ATG AAT TAC GAA GGC AGT CCA ATT AAA GTA ACA CTG          301
Glu Ala Glu Ala Met Asn Tyr Glu Gly Ser Pro Ile Lys Val Thr Leu
                 65                  70                  75

GCA ACT TTG AAA ATG TCT GTA CAG CCA ACG GTT TCC CTT GGG GGC TTT          349
Ala Thr Leu Lys Met Ser Val Gln Pro Thr Val Ser Leu Gly Gly Phe
             80                  85                  90

GAA ATA ACA CCA CCA GTG GTC TTA AGG TTG AAG TGT GGT TCA GGG CCA          397
Glu Ile Thr Pro Pro Val Val Leu Arg Leu Lys Cys Gly Ser Gly Pro
         95                  100                 105

GTG CAT ATT AGT GGA CAG CAC TTA GTA GTG TAC CGC CGG AAG CAC CAG          445
Val His Ile Ser Gly Gln His Leu Val Val Tyr Arg Arg Lys His Gln
110                 115                 120

GAG CTG CAA GCC ATG CAG ATG GAG CTG CAG AGC CCT GAG TAC AAG CTG          493
Glu Leu Gln Ala Met Gln Met Glu Leu Gln Ser Pro Glu Tyr Lys Leu
125                 130                 135                 140

AGC AAG CTC CGC ACC TCG ACC ATC ATG ACC GAC TAC AAC CCC AAC TAC          541
Ser Lys Leu Arg Thr Ser Thr Ile Met Thr Asp Tyr Asn Pro Asn Tyr
                145                 150                 155

TGC TTT GCT GGC AAG ACC TCC TCC ATC AGT GAC CTG AAG GAG GTG CCG          589
Cys Phe Ala Gly Lys Thr Ser Ser Ile Ser Asp Leu Lys Glu Val Pro
            160                 165                 170

CGG AAA AAC ATC ACC CTC ATT CGG GGT CTG GGC CAT GGC GCC TTT GGG          637
Arg Lys Asn Ile Thr Leu Ile Arg Gly Leu Gly His Gly Ala Phe Gly
        175                 180                 185

GAG GTG TAT GAA GGC CAG GTG TCC GGA ATG CCC AAC GAC CCA AGC CCC          685
Glu Val Tyr Glu Gly Gln Val Ser Gly Met Pro Asn Asp Pro Ser Pro
190                 195                 200

CTG CAA GTG GCT GTG AAG ACG CTG CCT GAA GTG TGC TCT GAA CAG GAC          733
Leu Gln Val Ala Val Lys Thr Leu Pro Glu Val Cys Ser Glu Gln Asp
205                 210                 215                 220

GAA CTG GAT TTC CTC ATG GAA GCC CTG ATC ATC AGC AAA TTC AAC CAC          781
Glu Leu Asp Phe Leu Met Glu Ala Leu Ile Ile Ser Lys Phe Asn His
                225                 230                 235

CAG AAC ATT GTT CGC TGC ATT GGG GTG AGC CTG CAA TCC CTG CCC CGG          829
Gln Asn Ile Val Arg Cys Ile Gly Val Ser Leu Gln Ser Leu Pro Arg
            240                 245                 250

TTC ATC CTG CTG GAG CTC ATG GCG GGG GGA GAC CTC AAG TCC TTC CTC          877
Phe Ile Leu Leu Glu Leu Met Ala Gly Gly Asp Leu Lys Ser Phe Leu
        255                 260                 265

CGA GAG ACC CGC CCT CGC CCG AGC CAG CCC TCC TCC CTG GCC ATG CTG          925
```

| | | | | | | | | | | | | | | | | |
|---|---|---|---|---|---|---|---|---|---|---|---|---|---|---|---|---|
|Arg|Glu|Thr|Arg|Pro|Arg|Pro|Ser|Gln|Pro|Ser|Ser|Leu|Ala|Met|Leu| |
| |270| | | |275| | | |280| | | | | | | |

| GAC | CTT | CTG | CAC | GTG | GCT | CGG | GAC | ATT | GCC | TGT | GGC | TGT | CAG | TAT | TTG | 973 |
|---|---|---|---|---|---|---|---|---|---|---|---|---|---|---|---|---|
| Asp | Leu | Leu | His | Val | Ala | Arg | Asp | Ile | Ala | Cys | Gly | Cys | Gln | Tyr | Leu | |
| 285 | | | | 290 | | | | | 295 | | | | | | 300 | |

| GAG | GAA | AAC | CAC | TTC | ATC | CAC | CGA | GAC | ATT | GCT | GCC | AGA | AAC | TGC | CTC | 1021 |
|---|---|---|---|---|---|---|---|---|---|---|---|---|---|---|---|---|
| Glu | Glu | Asn | His | Phe | Ile | His | Arg | Asp | Ile | Ala | Ala | Arg | Asn | Cys | Leu | |
| | | | | | 305 | | | | 310 | | | | | 315 | | |

| TTG | ACC | TGT | CCA | GGC | CCT | GGA | AGA | GTG | GCC | AAG | ATT | GGA | GAC | TTC | GGG | 1069 |
|---|---|---|---|---|---|---|---|---|---|---|---|---|---|---|---|---|
| Leu | Thr | Cys | Pro | Gly | Pro | Gly | Arg | Val | Ala | Lys | Ile | Gly | Asp | Phe | Gly | |
| | | | 320 | | | | | 325 | | | | | 330 | | | |

| ATG | GCC | CGA | GAC | ATC | TAC | AGG | GCG | AGC | TAC | TAT | AGA | AAG | GGA | GGC | TGT | 1117 |
|---|---|---|---|---|---|---|---|---|---|---|---|---|---|---|---|---|
| Met | Ala | Arg | Asp | Ile | Tyr | Arg | Ala | Ser | Tyr | Tyr | Arg | Lys | Gly | Gly | Cys | |
| | | 335 | | | | | 340 | | | | | 345 | | | | |

| GCC | ATG | CTG | CCA | GTT | AAG | TGG | ATG | CCC | CCA | GAG | GCC | TTC | ATG | GAA | GGA | 1165 |
|---|---|---|---|---|---|---|---|---|---|---|---|---|---|---|---|---|
| Ala | Met | Leu | Pro | Val | Lys | Trp | Met | Pro | Pro | Glu | Ala | Phe | Met | Glu | Gly | |
| | 350 | | | | | | 355 | | | | | 360 | | | | |

| ATA | TTC | ACT | TCT | AAA | ACA | GAC | ACA | TGG | TCC | TTT | GGA | GTG | CTG | CTA | TGG | 1213 |
|---|---|---|---|---|---|---|---|---|---|---|---|---|---|---|---|---|
| Ile | Phe | Thr | Ser | Lys | Thr | Asp | Thr | Trp | Ser | Phe | Gly | Val | Leu | Leu | Trp | |
| 365 | | | | | 370 | | | | | 375 | | | | | 380 | |

| GAA | ATC | TTT | TCT | CTT | GGA | TAT | ATG | CCA | TAC | CCC | AGC | AAA | AGC | AAC | CAG | 1261 |
|---|---|---|---|---|---|---|---|---|---|---|---|---|---|---|---|---|
| Glu | Ile | Phe | Ser | Leu | Gly | Tyr | Met | Pro | Tyr | Pro | Ser | Lys | Ser | Asn | Gln | |
| | | | | 385 | | | | | 390 | | | | | 395 | | |

| GAA | GTT | CTG | GAG | TTT | GTC | ACC | AGT | GGA | GGC | CGG | ATG | GAC | CCA | CCC | AAG | 1309 |
|---|---|---|---|---|---|---|---|---|---|---|---|---|---|---|---|---|
| Glu | Val | Leu | Glu | Phe | Val | Thr | Ser | Gly | Gly | Arg | Met | Asp | Pro | Pro | Lys | |
| | | | 400 | | | | | 405 | | | | | 410 | | | |

| AAC | TGC | CCT | GGG | CCT | GTA | TAC | CGG | ATA | ATG | ACT | CAG | TGC | TGG | CAA | CAT | 1357 |
|---|---|---|---|---|---|---|---|---|---|---|---|---|---|---|---|---|
| Asn | Cys | Pro | Gly | Pro | Val | Tyr | Arg | Ile | Met | Thr | Gln | Cys | Trp | Gln | His | |
| | | 415 | | | | | 420 | | | | | 425 | | | | |

| CAG | CCT | GAA | GAC | AGG | CCC | AAC | TTT | GCC | ATC | ATT | TTG | GAG | AGG | ATT | GAA | 1405 |
|---|---|---|---|---|---|---|---|---|---|---|---|---|---|---|---|---|
| Gln | Pro | Glu | Asp | Arg | Pro | Asn | Phe | Ala | Ile | Ile | Leu | Glu | Arg | Ile | Glu | |
| | 430 | | | | | 435 | | | | | 440 | | | | | |

| TAC | TGC | ACC | CAG | GAC | CCG | GAT | GTA | ATC | AAC | ACC | GCT | TTG | CCG | ATA | GAA | 1453 |
|---|---|---|---|---|---|---|---|---|---|---|---|---|---|---|---|---|
| Tyr | Cys | Thr | Gln | Asp | Pro | Asp | Val | Ile | Asn | Thr | Ala | Leu | Pro | Ile | Glu | |
| 445 | | | | | 450 | | | | | 455 | | | | | 460 | |

| TAT | GGT | CCA | CTT | GTG | GAA | GAG | GAA | GAG | AAA | GTG | CCT | GTG | AGG | CCC | AAG | 1501 |
|---|---|---|---|---|---|---|---|---|---|---|---|---|---|---|---|---|
| Tyr | Gly | Pro | Leu | Val | Glu | Glu | Glu | Glu | Lys | Val | Pro | Val | Arg | Pro | Lys | |
| | | | | 465 | | | | | 470 | | | | | 475 | | |

| GAC | CCT | GAG | GGG | GTT | CCT | CCT | CTC | CTG | GTC | TCT | CAA | CAG | GCA | AAA | CGG | 1549 |
|---|---|---|---|---|---|---|---|---|---|---|---|---|---|---|---|---|
| Asp | Pro | Glu | Gly | Val | Pro | Pro | Leu | Leu | Val | Ser | Gln | Gln | Ala | Lys | Arg | |
| | | | 480 | | | | | 485 | | | | | 490 | | | |

| GAG | GAG | GAG | CAG | CCC | AGC | TGC | CCC | ACC | ACC | TCT | GCC | TAC | CAC | CTC | CTC | 1597 |
|---|---|---|---|---|---|---|---|---|---|---|---|---|---|---|---|---|
| Glu | Glu | Glu | Gln | Pro | Ser | Cys | Pro | Thr | Thr | Ser | Ala | Tyr | His | Leu | Leu | |
| | | 495 | | | | | 500 | | | | | 505 | | | | |

| TGG | CAA | GGC | TGC | AAA | GAA | ACC | CAC | AGC | TGC | AGA | GGT | CTC | TGT | TCG | AGT | 1645 |
|---|---|---|---|---|---|---|---|---|---|---|---|---|---|---|---|---|
| Trp | Gln | Gly | Cys | Lys | Glu | Thr | His | Ser | Cys | Arg | Gly | Leu | Cys | Ser | Ser | |
| 510 | | | | | 515 | | | | | 520 | | | | | | |

| CCC | TAGAGGGCCG | GCCGTGGAAG | GGGACACGT | GAATATGGCA | TTCTCTCAGT | 1698 |
|---|---|---|---|---|---|---|
| Pro | | | | | | |
| 525 | | | | | | |

| CCAACCCTTC | TTCGGAGTTG | CACAAGGTCC | ACGGATCCAG | AAACAAGCCC | ACCAGCTTGT | 1758 |
|---|---|---|---|---|---|---|
| GGAACCCAAC | GTACGGCTCC | TGGTTTACAG | AGAAACCCAC | CAAAAAGAAT | AATCCTATAG | 1818 |
| CAAAGAAGGA | GCCACACGAC | AGGGGTAACC | TGGGGCTGGA | GGGAAGCTGT | ACTGTCCCAC | 1878 |
| CTAACGTTGC | AACTGGGAGA | CTTCCGGGGG | CCTCACTGCT | CCTAGACGCC | TCTTCGCTGA | 1938 |
| CTGCCAATAT | GAAGGAGGTA | CCTCTGTTCA | GGCTACGTCA | CTTCCCTTGT | GGGAATGTCA | 1998 |
| ATTACGGCTA | CCAGCAACAG | GGCTTGCCCT | TAGAAGCCGC | TACTGCCCCT | GGAGCTGGTC | 2058 |
| ATTACGAGGA | TACCATTCTG | AAAAGCAAGA | ATAGCATGAA | CCAGCCTGGG | CCCTGAGCTC | 2118 |

```
GGTCGCACAC TCACTTCTCT TCCTTGGGAT CCCTAAGACC GTGGAGGAGA GAGAGGCAAT      2178

GGCTCCTTCA CAAACCAGAG ACCAAATGTC ACGTTTTGTT TTGTGCCAAC CTATTTTGAA      2238

GTACCACCAA AAAAGCTGTA TTTTGAAAAT GCTTTAGAAA GGTTTTGAGC ATGGGTTCAT      2298

CCTATTCTTT CGAAAGAAGA AAATATCATA AAAATGAGTG ATAAATACAA GGCCCAGATG      2358

TGGTTGCATA AGGTTTTTAT GCATGTTTGT TGTATACTTC CTTATGCTTC TTTTAAATTG      2418

TGTGTGCTCT GCTTCAATCT AG                                              2440
```

(2) INFORMATION FOR SEQ ID NO:3:

(i) SEQUENCE CHARACTERISTICS:
        (A) LENGTH: 572 amino acids
        (B) TYPE: amino acid
        (D) TOPOLOGY: linear (ii) MOLECULE TYPE: protein (xi) SEQUENCE DESCRIPTION: SEQ ID NO:3:

```
Lys Ser Leu Gln Glu Gly Ala Thr Gly Gly His Ser Cys Pro Gln Ala
 1               5                  10                  15

Met Lys Lys Trp Gly Trp Glu Thr Arg Gly Gly Phe Gly Gly Gly Gly
                20                  25                  30

Gly Gly Cys Ser Ser Gly Gly Gly Gly Gly Gly Tyr Ile Gly Gly Asn
            35                  40                  45

Ala Ala Ser Asn Asn Asp Pro Glu Met Asp Gly Glu Asp Gly Val Ser
        50                  55                  60

Phe Ile Ser Pro Leu Gly Ile Leu Tyr Thr Pro Ala Leu Lys Val Met
 65                  70                  75                  80

Glu Gly His Gly Glu Val Asn Ile Lys His Tyr Leu Asn Cys Ser His
                85                  90                  95

Cys Glu Val Asp Glu Cys His Met Asp Pro Glu Ser His Lys Val Ile
               100                 105                 110

Cys Phe Cys Asp His Gly Thr Val Leu Ala Glu Asp Gly Val Ser Cys
           115                 120                 125

Ile Val Ser Pro Thr Pro Glu Pro His Leu Pro Leu Ser Leu Ile Leu
       130                 135                 140

Ser Val Val Thr Ser Ala Leu Val Ala Ala Leu Val Leu Ala Phe Ser
145                 150                 155                 160

Gly Ile Met Ile Val Tyr Arg Arg Lys His Gln Glu Leu Gln Ala Met
                165                 170                 175

Gln Met Glu Leu Gln Ser Pro Glu Tyr Lys Leu Ser Lys Leu Arg Thr
            180                 185                 190

Ser Thr Ile Met Thr Asp Tyr Asn Pro Asn Tyr Cys Phe Ala Gly Lys
        195                 200                 205

Thr Ser Ser Ile Ser Asp Leu Lys Glu Val Pro Arg Lys Asn Ile Thr
    210                 215                 220

Leu Ile Arg Gly Leu Gly His Gly Ala Phe Gly Glu Val Tyr Glu Gly
225                 230                 235                 240

Gln Val Ser Gly Met Pro Asn Asp Pro Ser Pro Leu Gln Val Ala Val
                245                 250                 255

Lys Thr Leu Pro Glu Val Cys Ser Glu Gln Asp Glu Leu Asp Phe Leu
            260                 265                 270

Met Glu Ala Leu Ile Ile Ser Lys Phe Asn His Gln Asn Ile Val Arg
        275                 280                 285

Cys Ile Gly Val Ser Leu Gln Ser Leu Pro Arg Phe Ile Leu Leu Glu
```

|     |     |     |     | 290 |     |     |     |     | 295 |     |     |     |     | 300 |     |
| --- | --- | --- | --- | --- | --- | --- | --- | --- | --- | --- | --- | --- | --- | --- | --- |
| Leu | Met | Ala | Gly | Gly | Asp | Leu | Lys | Ser | Phe | Leu | Arg | Glu | Thr | Arg | Pro |
| 305 |     |     |     |     | 310 |     |     |     |     | 315 |     |     |     |     | 320 |
| Arg | Pro | Ser | Gln | Pro | Ser | Ser | Leu | Ala | Met | Leu | Asp | Leu | Leu | His | Val |
|     |     |     |     | 325 |     |     |     |     | 330 |     |     |     |     | 335 |     |
| Ala | Arg | Asp | Ile | Ala | Cys | Gly | Cys | Gln | Tyr | Leu | Glu | Glu | Asn | His | Phe |
|     |     |     | 340 |     |     |     |     | 345 |     |     |     |     | 350 |     |     |
| Ile | His | Arg | Asp | Ile | Ala | Ala | Arg | Asn | Cys | Leu | Leu | Thr | Cys | Pro | Gly |
|     |     | 355 |     |     |     |     | 360 |     |     |     |     | 365 |     |     |     |
| Pro | Gly | Arg | Val | Ala | Lys | Ile | Gly | Asp | Phe | Gly | Met | Ala | Arg | Asp | Ile |
|     | 370 |     |     |     |     | 375 |     |     |     |     | 380 |     |     |     |     |
| Tyr | Arg | Ala | Ser | Tyr | Tyr | Arg | Lys | Gly | Gly | Cys | Ala | Met | Leu | Pro | Val |
| 385 |     |     |     |     | 390 |     |     |     |     | 395 |     |     |     |     | 400 |
| Lys | Trp | Met | Pro | Pro | Glu | Ala | Phe | Met | Glu | Gly | Ile | Phe | Thr | Ser | Lys |
|     |     |     |     | 405 |     |     |     |     | 410 |     |     |     |     | 415 |     |
| Thr | Asp | Thr | Trp | Ser | Phe | Gly | Val | Leu | Leu | Trp | Glu | Ile | Phe | Ser | Leu |
|     |     |     | 420 |     |     |     |     | 425 |     |     |     |     | 430 |     |     |
| Gly | Tyr | Met | Pro | Tyr | Pro | Ser | Lys | Ser | Asn | Gln | Glu | Val | Leu | Glu | Phe |
|     |     | 435 |     |     |     |     | 440 |     |     |     |     | 445 |     |     |     |
| Val | Thr | Ser | Gly | Gly | Arg | Met | Asp | Pro | Pro | Lys | Asn | Cys | Pro | Gly | Pro |
|     | 450 |     |     |     |     | 455 |     |     |     |     | 460 |     |     |     |     |
| Val | Tyr | Arg | Ile | Met | Thr | Gln | Cys | Trp | Gln | His | Gln | Pro | Glu | Asp | Arg |
| 465 |     |     |     |     | 470 |     |     |     |     | 475 |     |     |     |     | 480 |
| Pro | Asn | Phe | Ala | Ile | Ile | Leu | Glu | Arg | Ile | Glu | Tyr | Cys | Thr | Gln | Asp |
|     |     |     |     | 485 |     |     |     |     | 490 |     |     |     |     | 495 |     |
| Pro | Asp | Val | Ile | Asn | Thr | Ala | Leu | Pro | Ile | Glu | Tyr | Gly | Pro | Leu | Val |
|     |     |     | 500 |     |     |     |     | 505 |     |     |     |     | 510 |     |     |
| Glu | Glu | Glu | Glu | Lys | Val | Pro | Val | Arg | Pro | Lys | Asp | Pro | Glu | Gly | Val |
|     |     |     | 515 |     |     |     | 520 |     |     |     |     | 525 |     |     |     |
| Pro | Pro | Leu | Leu | Val | Ser | Gln | Gln | Ala | Lys | Arg | Glu | Glu | Glu | Gln | Pro |
|     | 530 |     |     |     |     | 535 |     |     |     |     | 540 |     |     |     |     |
| Ser | Cys | Pro | Thr | Thr | Ser | Ala | Tyr | His | Leu | Leu | Trp | Gln | Gly | Cys | Lys |
| 545 |     |     |     |     | 550 |     |     |     |     | 555 |     |     |     |     | 560 |
| Glu | Thr | His | Ser | Cys | Arg | Gly | Leu | Cys | Ser | Ser | Pro |     |     |     |     |
|     |     |     |     | 565 |     |     |     |     | 570 |     |     |     |     |     |     |

( 2 ) INFORMATION FOR SEQ ID NO:4:

( i ) SEQUENCE CHARACTERISTICS:
        ( A ) LENGTH: 525 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Glu | Asp | Ser | Met | Asp | Met | Asp | Met | Ser | Pro | Leu | Arg | Pro | Gln | Asn |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Tyr | Leu | Phe | Gly | Cys | Glu | Leu | Lys | Ala | Asp | Lys | Asp | Tyr | His | Phe | Lys |
|     |     |     | 20 |     |     |     |     | 25 |     |     |     |     | 30 |     |     |
| Val | Asp | Asn | Asp | Glu | Asn | Glu | His | Gln | Leu | Ser | Leu | Arg | Thr | Val | Ser |
|     |     |     | 35 |     |     |     |     | 40 |     |     |     |     | 45 |     |     |
| Leu | Gly | Ala | Gly | Ala | Lys | Asp | Glu | Leu | His | Ile | Val | Glu | Ala | Glu | Ala |
|     |     | 50 |     |     |     |     | 55 |     |     |     |     | 60 |     |     |     |
| Met | Asn | Tyr | Glu | Gly | Ser | Pro | Ile | Lys | Val | Thr | Leu | Ala | Thr | Leu | Lys |
| 65 |     |     |     |     | 70 |     |     |     |     | 75 |     |     |     |     | 80 |

```
Met Ser Val Gln Pro Thr Val Ser Leu Gly Gly Phe Glu Ile Thr Pro
                85                  90                  95
Pro Val Val Leu Arg Leu Lys Cys Gly Ser Gly Pro Val His Ile Ser
            100                 105                 110
Gly Gln His Leu Val Val Tyr Arg Arg Lys His Gln Glu Leu Gln Ala
        115                 120                 125
Met Gln Met Glu Leu Gln Ser Pro Glu Tyr Lys Leu Ser Lys Leu Arg
    130                 135                 140
Thr Ser Thr Ile Met Thr Asp Tyr Asn Pro Asn Tyr Cys Phe Ala Gly
145                 150                 155                 160
Lys Thr Ser Ser Ile Ser Asp Leu Lys Glu Val Pro Arg Lys Asn Ile
                165                 170                 175
Thr Leu Ile Arg Gly Leu Gly His Gly Ala Phe Gly Glu Val Tyr Glu
            180                 185                 190
Gly Gln Val Ser Gly Met Pro Asn Asp Pro Ser Pro Leu Gln Val Ala
        195                 200                 205
Val Lys Thr Leu Pro Glu Val Cys Ser Glu Gln Asp Glu Leu Asp Phe
    210                 215                 220
Leu Met Glu Ala Leu Ile Ile Ser Lys Phe Asn His Gln Asn Ile Val
225                 230                 235                 240
Arg Cys Ile Gly Val Ser Leu Gln Ser Leu Pro Arg Phe Ile Leu Leu
                245                 250                 255
Glu Leu Met Ala Gly Gly Asp Leu Lys Ser Phe Leu Arg Glu Thr Arg
            260                 265                 270
Pro Arg Pro Ser Gln Pro Ser Ser Leu Ala Met Leu Asp Leu Leu His
        275                 280                 285
Val Ala Arg Asp Ile Ala Cys Gly Cys Gln Tyr Leu Glu Glu Asn His
    290                 295                 300
Phe Ile His Arg Asp Ile Ala Ala Arg Asn Cys Leu Leu Thr Cys Pro
305                 310                 315                 320
Gly Pro Gly Arg Val Ala Lys Ile Gly Asp Phe Gly Met Ala Arg Asp
                325                 330                 335
Ile Tyr Arg Ala Ser Tyr Tyr Arg Lys Gly Gly Cys Ala Met Leu Pro
            340                 345                 350
Val Lys Trp Met Pro Pro Glu Ala Phe Met Glu Gly Ile Phe Thr Ser
        355                 360                 365
Lys Thr Asp Thr Trp Ser Phe Gly Val Leu Leu Trp Glu Ile Phe Ser
    370                 375                 380
Leu Gly Tyr Met Pro Tyr Pro Ser Lys Ser Asn Gln Glu Val Leu Glu
385                 390                 395                 400
Phe Val Thr Ser Gly Gly Arg Met Asp Pro Pro Lys Asn Cys Pro Gly
                405                 410                 415
Pro Val Tyr Arg Ile Met Thr Gln Cys Trp Gln His Gln Pro Glu Asp
            420                 425                 430
Arg Pro Asn Phe Ala Ile Ile Leu Glu Arg Ile Glu Tyr Cys Thr Gln
        435                 440                 445
Asp Pro Asp Val Ile Asn Thr Ala Leu Pro Ile Glu Tyr Gly Pro Leu
    450                 455                 460
Val Glu Glu Glu Glu Lys Val Pro Val Arg Pro Lys Asp Pro Glu Gly
465                 470                 475                 480
Val Pro Pro Leu Leu Val Ser Gln Gln Ala Lys Arg Glu Glu Glu Gln
                485                 490                 495
Pro Ser Cys Pro Thr Thr Ser Ala Tyr His Leu Leu Trp Gln Gly Cys
            500                 505                 510
```

```
            Lys  Glu  Thr  His  Ser  Cys  Arg  Gly  Leu  Cys  Ser  Ser  Pro
                      515                      520                      525
```

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: both
        ( D ) TOPOLOGY: linear ( i i ) MOLECULE TYPE: DNA ( x i ) SEQUENCE DESCRIPTION: SEQ ID NO:5:

```
TCCCTTGGGG  GCTTTGAAAT  AACACC                                            26
```

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: DNA ( x i ) SEQUENCE DESCRIPTION: SEQ ID NO:6:

```
GCTGAGCAAG  CTCCGCACCT  CG                                                22
```

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: DNA ( x i ) SEQUENCE DESCRIPTION: SEQ ID NO:7:

```
GCTGAGCAAG  CTCCGCACCT  CG                                                22
```

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: both
        ( D ) TOPOLOGY: linear ( i i ) MOLECULE TYPE: DNA ( x i ) SEQUENCE DESCRIPTION: SEQ ID NO:8:

```
GCTACCACCT  CCAGGGGCAG  A                                                 21
```

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: both
        ( D ) TOPOLOGY: linear ( i i ) MOLECULE TYPE: DNA ( x i ) SEQUENCE DESCRIPTION: SEQ ID NO:9:

```
AGCACTTAGT  AGCTGTGGAG  GAAG                                              24
```

(2) INFORMATION FOR SEQ ID NO:10:

(i) SEQUENCE CHARACTERISTICS:
(A) LENGTH: 24 base pairs
(B) TYPE: nucleic acid
(C) STRANDEDNESS: both
(D) TOPOLOGY: linear (ii) MOLECULE TYPE: DNA (xi) SEQUENCE DESCRIPTION: SEQ ID NO:10:

AGCACTTAGT AGTGTACCGC CGGA  24

NUCLEIC ACID SEQUENCES AND FUSION PROTEINS PRESENT IN HUMAN T(2;5) LYMPHOMA

Part of the work performed in this invention was made with the use of government funding by way of grants from the National Institutes of Health and National Cancer Institute, Grant Nos. K08CA01702, P01CA20180, P30CA21765. Therefore, the government has certain rights in this invention.

FIELD OF THE INVENTION

The present invention is directed to the field of cancer diagnosis and therapy. Specifically, the present invention relates to methods of detecting and treating human t(2;5) positive lymphoma.

BACKGROUND OF THE INVENTION

Large cell lymphomas comprise approximately one fourth of all non-Hodgkin's lymphomas in children and young adults. Approximately one third of these tumors have a t(2;5)(p23;q35) chromosomal translocation (H. Stein and F. Dallenbach, in Neoplastic Hematopathology, D. M. Knowles, Ed. (Williams & Wilkins, Baltimore pp. 675–714 (1992)), suggesting that rearrangement of cellular proto-oncogenes on these chromosomes contributes to lymphomagenesis. Lymphomas with the t(2;5) typically involve lymph nodes, skin, lung, soft tissue, bone and the gastrointestinal tract, and arise predominantly from activated T lymphocytes (Y. Kaneko et al., Blood. 73: 806 (1989); M. M. Le Beau et al., Leukemia 3:866 (1989); R. Rimokh et al., Br. J. Haematol. 71:31 (1989); D. Y. Mason et al., Br. J. Haematol. 74:161 (1990); M. A. Bitter Am. J. Surg. Pathol. 14:305 (1990); M. E. Kadin, J. Clin. Oncol. 9:533 (1991); J. P. Greer et al., J. Clin. Oncol. 9:539 (1991); V. Vecchi et al., Med. Pediatr. Oncol. 21:402 (1993)). The malignant cells express IL-2 receptors and CD30 (Ki-1) antigen, a receptor for a newly described member of the tumor necrosis factor ligand family (H. Durkop et al., Cell 68:421 (1992); C. A. Smith et al., Cell 73:1349 (1993)). By the updated Kiel lymphoma classification, most tumors with the t(2;5) are classified as anaplastic large cell non-Hodgkin's lymphomas (A. G. Stansfeld et al., Lancet. 1:292 (1988)).

Chromosomal abnormalities are frequently associated with malignant diseases. In a number of instances, specific chromosomal translocations have been characterized, which generate fusion genes encoding proteins with oncogenic properties (Sawyers et al., Cell 64:337–350 (1991)). A specific t(2;5) translocation is the hallmark of human anaplastic large cell non-Hodgkin's lymphoma.

SUMMARY OF THE INVENTION

Disclosed herein is the cloning and sequencing of the human nucleic acid sequences which are rearranged in the t(2;5)(p23;q35) chromosomal translocation event which occurs in human t(2;5) lymphoma. The rearrangement was found to bring sequences from the nucleolar phosphoprotein gene (the NPM gene) on chromosome 5q35 to those from a previously unidentified protein tyrosine kinase gene (hereinafter the ALK gene) on chromosome 2p23. The sequence of the fusion gene and fusion protein are also disclosed (hereinafter the NPM/ALK fusion gene or protein, respectively).

Utilizing the sequences of the identified NPM/ALK fusion gene, the present invention provides methods of identifying the presence of nucleic acid sequence in a sample which contains the NPM/ALK fusion sequence which comprises the steps of:

contacting a sample with two nucleic acid amplification primers, wherein a first nucleic acid amplification primer is capable of hybridizing to the nucleic acid sequence encoding NPM or a complementary sequence thereof, and a second nucleic acid primer which is capable of hybridizing to a nucleic acid sequence encoding ALK or a complementary sequence thereof;

amplifying the primed sequences in the sample which hybridizes to the two primers; and detecting the presence of amplified nucleic acid sequence in the sample which contain the NPM/ALK fusion.

The present invention provides alternative methods for identifying the presence of a nucleic acid sequence in a sample which contains the NPM/ALK fusion which comprises the steps of:

contacting a sample with two nucleic acid probes, wherein the first nucleic acid probe is capable of hybridizing to the nucleic acid sequence encoding NPM, and a second nucleic acid probe is capable of hybridizing to the nucleic acid sequence encoding ALK; and detecting the presence of a nucleic acid sequence in the sample which hybridize to both the first and the second nucleic acid probes.

Alternatively, a single nucleic acid probe which spans the NPM/ALK fusion junction can be used in place of the two separate probes.

The present invention further provides methods of detecting the presence of the NPM/ALK fusion which are based on antibody detection systems. Specifically, since a NPM/ALK fusion protein is expressed in t(2:5) lymphoma cells, antibodies which identify the fusion protein can be used to detect the presence of the NPM/ALK fusion protein. For example, the NPM/ALK fusion protein can be detected by;

contacting a sample with two antibodies, wherein a first antibody is capable of binding to NPM, and a second antibody is capable of binding to ALK; and detecting the presence of a protein in the sample which binds both the first and the second antibodies.

In addition, due to the nature of the fusion protein created in the NPM/ALK fusion, a single antibody which binds selectively the fusion protein can be generated and used to identify NPM/ALK fusion.

The invention further provides compartmentalized kits to receive in close confinement one or more containers containing the reagents used in the above described detection methods.

with a 5' NPM cDNA fragment (top panel) and a 3' fragment from the NPM-ALK cDNA (pS1.2) (bottom panel) (The faint, approximately 4 kb bands evident in the t(2;5)-positive cell line RNAs that were hybridized with pS1.2 represent cross-hybridization of this probe with the 28S ribosomal RNA; such bands were not apparent in hybridizations of poly (A)+RNA). Twenty micrograms of total RNA was loaded in each sample lane, with the exception of Rh30 [8 μg poly (A)+]. (C) Analysis of RNAs [2 μg poly (A)+per lane; Clontech, San Diego, Calif.] from various adult and fetal human tissues with a 3' NPM-ALK cDNA probe (pS1.2). Open circles, 6.5 kb ALK transcripts; closed circles, 8.0 kb transcripts; open square, 4.4 kb transcript; arrowheads, 6.0 kb transcripts. Hybridization results obtained with a β-actin cDNA probe are shown in the lower panel. The panels hybridized with pS1.2 represent 6-day autoradiographic exposures; the β-actin hybridizations were exposed for 4 hr.

FIG. 2 (Panels A–C): Deduced amino acid sequence of (A) NPM-ALK and (B) the portion of ALK immediately adjacent to the fusion junction, and (C) homology comparison of the catalytic domain of ALK with other tyrosine kinases of the insulin receptor subfamily. In panel A, solid circles indicate possible protein kinase C phosphorylation sites; dashed underline, potential metal-binding domain; arrows, boundaries of the ALK catalytic domain; asterisks, conserved residues of the consensus ATP recognition sequence and the ATP-binding lysine residue; solid underlines, consensus sequences specific for tyrosine kinases. In panel B, arrow, position in normal ALK at which NPM-ALK fusion occurs; box, residues (hydrophobicity greater than 1.5) comprising a putative transmembrane domain. In panel C, the amino acid residues of the tyrosine kinase catalytic domains are aligned, with gaps indicated by dashes. Shaded boxes indicate residues in the related tyrosine kinases that are identical to amino acids of ALK. All sequences are for human proteins, excluding 7les (*Drosophila melanogaster* Sevenless) (J. J. Krolewski et al., EMBO J. 10:2911 (1991); H. Toyoshima et al., Proc. Natl. Acad. Sci. U.S.A. 90:5404 (1993); D. Martin-Zanca et al., Nature 319:743 (1986); H. Matsushime et al., Mol. Cell. Biol. 6:3000 (1986); J. M. Chen et al., Oncogene. 6:257 (1991); K. Basler et al., Cell 54:299 (1988); D. D. Bowtell et al., Genes and Development 2:620 (1988); A. Ullrich et al., EMBO J. 5:2503 (1986); A. Ullrich et al., Nature 313:756 (1985); Y. Ebina et al., Cell 40:747 (1985)).

Figure 3A:
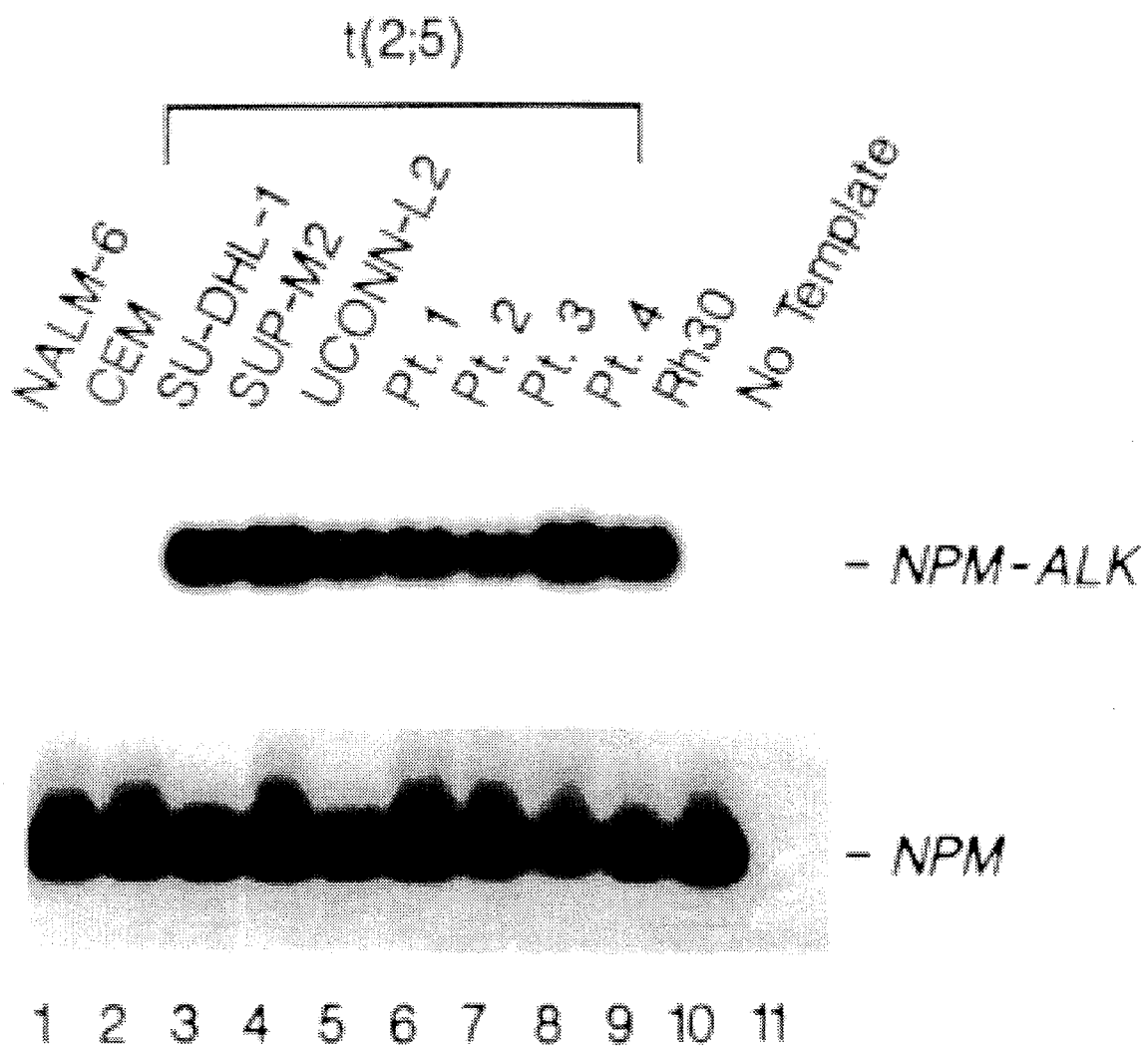

FIG. 3 (Panels A–C): (A) Southern blot analysis of NPM-ALK and NPM RNA-PCR products. Total RNAs (1 μg) from t(2;5)-positive cell lines (SU-DHL-1, SUP-M2 and UCONN-L2; lanes 3–5) and diagnostic samples (Pts. 1–4, lanes 6–9) were analyzed; in addition, RNAs from the t(2;5)-negative B- and T-lymphoid leukemia cell lines (NALM-6 and CEM, respectively; lanes 1,2) and the Rh30 rhabdomyosarcoma cell line (lane 10), which lacks the translocation but expresses normal ALK, were included as negative controls, as was a blank without RNA (lane 11). (B) Nucleotide sequence of the NPM-ALK RNA-PCR product. Single underlines, sequences homologous (5' end) or complementary (3' end) to the primers used for amplification; double underline, sequences homologous to the detection oligonucleotide used as a probe for Southern hybridization; vertical line, fusion junction between NPM and ALK. (C) Schematic representations of the proteins encoded by normal NPM, the NPM-ALK fusion gene and normal ALK. Arrows indicate the position of the NPM-ALK fusion junction and the corresponding positions in NPM and ALK; MB, potential metal-binding domain; AC, acidic amino acid clusters; N, nuclear localization signals; Tm, location of the putative transmembrane domain of normal ALK. NPM phosphorylation sites are also indicated (solid circles, protein kinase C; open circle, nucleolar type II kinase; asterisks, cdc2 kinase). The two protein kinase C phosphorylation sites in the NPM amino terminus are potential sites only; all other sites have been demonstrated in vitro or in vivo (M. Peter et al., Cell 60:791 (1990); P. K. Chan et al., Biochem. J. 270:549 (1990); R. Beckmann et al., Eur. J. Biochem. 210:45 (1992)). The portion of ALK that has not been fully characterized is shown within dashed lines.

DETAILED DESCRIPTION OF THE INVENTION

The present invention is based on the identification of the nucleic acid sequence which is present as a result of the translocation event associated with human t(2;5) lymphoma (hereinafter the NPM/ALK fusion gene), the identification of a novel protein tyrosine kinase gene on chromosome 2p23 (hereinafter the ALK gene and protein), the identification of mRNA containing a fusion of the nucleolar phosphoprotein gene (hereinafter NPM) and the ALK gene which is present in t(2;5) lymphoma cells, and the identification of an open reading frame within the NPM/ALK fusion mRNA which encodes a novel fusion protein product (hereinafter the NPM/ALK fusion protein).

Based on these observations, one embodiment of the present invention provides an isolated nucleic acid sequence which encodes the partial ALK protein (Seq. ID. No. 1), an isolated nucleic acid sequence which encodes the NPM/ALK fusion protein (Seq. ID. No. 2), an isolated partial ALK protein (Seq ID No. 3), and an isolated NPM/ALK fusion protein (Seq. ID No. 4).

Specifically, the partial amino acid sequence of the ALK protein is presented in FIG. 2b and c (Seq. ID No. 3), the partial nucleic acid sequence encoding ALK is presented in Seq. ID No. 1, the amino acid sequence of NPM/ALK fusion protein is presented in FIG. 2a (Seq. ID No. 4), the amino acid sequence of ALK resides immediately adjacent to the NPM/ALK fusion junction is presented in FIG. 2b (Seq. ID No. 7), and the nucleic acid sequence encoding the NPM/ALK fusion junction is presented in FIG. 3b (Seq. ID Nos. 2 and 4). A clone containing the ALK cDNA has been deposited under the terms of the Budapest Treaty at the ATCC as ATCC 69497.

By inserting any of the nucleic acid sequences of the present invention into an appropriate vector, one skilled in the art can readily produce large quantities of the specific sequence. Alternatively, the nucleic acid sequences of the present invention can be inserted into an expression vector in order to produce the amino acid sequences of the present invention.

There are numerous host/vectors systems available for the propagation of nucleic acid sequences and/or the production of expressed proteins. These include, but are not limited to, plasmid and vital vectors, and prokaryotic and eukaryotic host. One skilled in the art can readily adapt any host/vector system which is capable of propagating or expressing heterologous DNA to produce or express the sequences of the present invention.

In Example 1, the present invention provides evidence that the nucleic acid sequences containing the NPM/ALK fusion sequence are present in patients with t(2;5) lymphoma. Based on this observation, the present invention provides methods of assaying for the presence of nucleic acid sequences containing the NPM/ALK fusion in a sample and thus provides an assay for the detection of t(2;5) lymphoma.

One example of the assay methods of the present invention which are used to detect NPM/ALK fusions are based on the preferential amplification of sequences within a sample which contain the nucleic acid sequence encoding the NPM/ALK fusion protein.

In general, an amplification reaction such as the polymerase chain reaction (PCR) is used to amplify either the mRNA encoding the NPM/ALK fusion protein, or the genomic DNA which contains the t(2;5) translocation. Specifically, utilizing the sequences of the identified fusion gene, the present invention provides methods of identifying the presence of a nucleic acid sequence in a sample which contains the NPM/ALK fusion sequence comprising the steps of:

contacting a sample with two nucleic acid amplification primers, wherein a first nucleic acid amplification primer is capable of hybridizing to the nucleic acid sequence encoding NPM or a complementary sequence thereof, and a second nucleic acid amplification primer which is capable of hybridizing to the nucleic acid sequence encoding ALK or a complementary sequence thereof;

amplifying the primed nucleic acid sequences in the sample; and detecting the presence of amplified nucleic acid sequence in the sample which contains the NPM/ALK fusion sequence.

As used herein, an amplification primer is any short DNA sequence which can hybridize to a target sequence and allow the target sequence to be amplified when incubated with the appropriate reagents under the appropriate condition. For example see Ausubel et al., Current Protocols in Molecular Biology, Wiley Press (1993). Amplification requires the use of two primers which flank the region which is to be amplified. One primer hybridizes to the target sequence while the other primer hybridizes to a sequence complementary to the target sequence.

In the present invention, one of the amplification primers is derived from the sequence of NPM gene while the second primer is derived from the sequence of the ALK gene. Any fragment of the NPM or ALK gene sequences can be used to generate the appropriate amplification primers so long as the fragments of the sequence which are chosen are present in the NPM/ALK fusion gene. In Example 1, Seq ID No. 5 and the reverse complementary sequence of Seq. ID No. 6 were chosen as primers. One skilled in the art will readily recognize that other fragments of the NPM and ALK genes can be used as primers in order to obtain similar results.

The target sequence which is to be amplified can either be the mRNA which encodes the NPM/ALK fusion protein or can be genomic DNA which contains the t(2;5) translocation. A skilled artisan can readily employ techniques known in the art to prepare a sample containing the appropriate target molecule.

As used herein, an amplification primer is said to be capable of hybridizing to a nucleic acid sequence if the primer is capable of forming hydrogen bonds with the target sequence under appropriate condition. In general the preferred condition are characterized as being high stringency condition. A skilled artisan can readily determine the appropriate conditions following methods described elsewhere (PCR Protocols, Cold Spring Harbor Press (1991), Privitera et al., Blood 79:1781 (1992)).

As used herein, amplification refers to the process of generating multiple copies of a target sequence. Various methods and enzymes are available to accomplish this goal. In the preferred embodiment, Taq-1 DNA polymerase is used in the method known as PCR to amplify the target sequence (see Example 1). However, a skilled artisan can substitute other enzymes for the Taq-1 polymerase so long as the amplification goal is achieved.

As used herein, detecting the amplified target sequence refers to any method which can be employed to determine the presence or absence of an amplified nucleic acid sequence of a given size or a particular sequence. In one application, the amplification product is subjected to agarose or acrylamide gel electrophoresis to resolve the various sizes of nucleic acids which are present in the amplified sample. The resulting gel can then be analyzed visually using a nucleic acid stain, for example ethidium bromide, to determine if an appropriately sized nucleic acid molecule is present in the amplified sample.

Alternatively, a delectably labeled probe can be employed to determine if the sample contains the amplified sequence (See Example 1). Such a probe can be used following the above described electrophoresis, or can be used in a dot blot or in situ assay method. The generation of a detection probe based on the NPM/ALK fusion gene is described in detail below.

In addition to methods which rely on the amplification of a target sequence, the present invention further provides methods for identifying nucleic acids containing the NPM/ALK fusions which do not require sequence amplification. Specifically, the known methods of Southern and Northern blot hybridization can be employed to determine if a sample contains the NPM/ALK nucleic acid fusion sequence (Sambrook et al., Molecular Cloning ed. Spring Harbor Press (1989)). In detail, such fusions can be detected by:

contacting a sample with two nucleic acid probes, wherein a first nucleic acid probe is capable of hybridizing to the nucleic acid sequence encoding NPM, and a second nucleic acid probe is capable of hybridizing to the nucleic acid sequence encoding ALK; and detecting the presence of a nucleic acid sequence within the sample which hybridizes to both the first and the second nucleic acid probes.

The nucleic acid probes of the present invention include DNA as well as RNA probes, such probes being generated using techniques known in the art (Sambrook et al., Molecular Cloning ed. Spring Harbor Press (1989)). A skilled artisan can employ such known techniques using the NPM and ALK gene sequences herein described, or fragments thereof, as probes.

In another application of the above described method, a single nucleic acid probe, as opposed to two separate probes, spanning the fusion region of the NPM/ALK fusion, is employed in the Southern or Northern assay system.

Specifically, such a method comprises the steps of:

contacting a sample with a single nucleic acid probe, wherein the nucleic acid probe is capable of hybridizing to the fusion junction of the NPM/ALK fusion gene; and detecting the presence of nucleic acid sequences in the sample which hybridizes to the nucleic acid probe.

Alternatively, a single probe can be designed which is based on either the ALK, NPM or NPM/ALK fusion sequence. Such a probe will correspond to a restriction enzyme fragment of NPM or ALK whose size is altered as a result of the rearrangement (restriction fragment length polymorphism, RFLP analysis).

Any method known in the art can be utilized to label the probes used in the above assay methods. In the two probe embodiment, the first and the second probe can be labeled with different radioisotopes, enzymes or chromophores. Using the differently labeled probes, one can identify DNA sequences which bind one or both of the probes. In another application, the first and the second probe can be labeled in such a fashion that a signal is produced when the probes hybridize to the same nucleic acid fragment. Such a procedure is described in U.S. Pat. No. 4,820,630.

In one application of the above described method, one of the nucleic acid probes is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The samples used in the detection methods of the present invention include, but are not limited to, cells or tissues, protein, membrane, or nucleic acid extracts of the cells or tissues, and biological fluids such as blood, serum, and plasma. The sample used in the above-described method will vary based on the assay format, nature of the detection method, and the tissues, cells or extracts which are used as the sample. Methods for preparing protein extracts, membrane extracts or nucleic acid extracts of cells are well known in the art and can be readily be adapted in order to obtain a sample which is compatible with the method utilized.

One preferred type of sample which can be utilized in the present invention is derived from isolated lymphoma cells. Such cells can be used to prepare a suitable extract or can be used in procedures based on in situ analysis. An example of in situ analysis is referred to as fluorescence in situ hybridization (FISH) and is described in detail in Example 1 and by Selleri et al. PNAS 88:887–891 (1991) and Tkachuk et al. Science 250:559–562 (1990).

The present invention further provides methods of detecting NPM/ALK fusions which rely on the ability of an antibody to selectively bind to a specific antigen.

In one embodiment, a NPM/ALK fusion protein is detected using two sets of antibodies, one set comprising an antibody capable of binding to the NPM protein and the other set comprising an antibody capable of binding to the ALK protein.

Specifically, such a method comprises the steps of:

contacting a sample with two antibodies, wherein a first antibody is capable of binding to NPM, and a second antibody is capable of binding to ALK; and detecting the presence of proteins in the sample which bind to both the first and the second antibody.

The antibodies utilized in the above methods can be monoclonal or polyclonal antibodies, as well fragments of these antibodies. In general, techniques for preparing monoclonal antibodies are well known in the art (Campbell, A. M., "Monoclonal Antibody Technology: Laboratory Techniques in Biochemistry and Molecular Biology," Elsevier Science Publishers, Amsterdam, The Netherlands (1984); St. Groth et al., J. Immunol. Methods 35:1–21 (1980). For example, an antibody capable of binding the NPM or ALK protein can be generated by immunizing an animal with a polypeptide whose sequence is obtained from a region of the NPM or ALK proteins which are present in the NPM/ALK fusion protein.

Any animal (mouse, rabbit, etc.) which is known to produce antibodies can be utilized to produce antibodies with the desired specificity. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide selected, and the site of injection. The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For generating monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109–124 (1988)).

Hybridomas secreting the desired antibodies are cloned and the class and subclass are determined using procedures known in the art (Campbell, A. M., Monoclonal Antibody Technology: Laboratory Techniques in Biochemistry and Molecular Biology, Elsevier Science Publishers, Amsterdam, The Netherlands (1984)).

For polyclonal antibodies, antibody containing antisera is isolated from the immunized animal and is screened for the presence of antibodies with the desired specificity using one of the above-described procedures.

Conditions for incubating an antibody with a test sample vary. Incubating conditions depend on the format employed for the assay, the detection methods employed, the nature of the test sample, and the type and nature of the antibody used in the assay. One skilled in the art will recognize that any one of the commonly available immunological assay formats (such as radioimmunoassays, enzyme-linked immunosorbent assays, diffusion based ouchterlony, or rocket immunofluorescent assays) can readily be adapted to employ the antibodies of the present invention. Examples of such assays can be found in Chard, T. "An Introduction to Radioimmunoassay and Related Techniques" Elsevier Science Publishers, Amsterdam, The Netherlands (1986); Bullock, G. R. et al., "Techniques in Immunocytochemistry," Academic Press, Orlando, Fla. Vol. 1 (1982), Vol. 2 (1983), Vol. 3 (1985); Tijssen, P., "Practice and Theory of Enzyme Immunoassays: Laboratory Techniques in Biochemistry and Molecular Biology," Elsevier Science Publishers, Amsterdam, The Netherlands (1985).

In one embodiment of the above described method either the anti-NPM antibody or the anti-ALK antibody is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling antibodies to such solid supports are well known in the art (Weir, D. M. et al., "Handbook of Experimental Immunology" 4th Ed., Blackwell Scientific Publications, Oxford, England, Chapter 10 (1986), Jacoby, W. D. et al., Meth. Enzym. 34 Academic Press, N.Y. (1974).

Additionally, one or more of the antibodies used in the above described methods can be detectably labelled prior to use. Antibodies can be detectably labelled through the use of radioisotopes, affinity labels (such as biotin, avidin, etc.), enzymatic labels (such as horse radish peroxidase, alkaline phosphatase, etc.) fluorescent labels (such as FITC or rhodamine, etc.), paramagnetic atoms, etc. Procedures for accomplishing such labelling are well-known in the art, for example see Sternberger, L. A. et al., J. Histochem. Cytochem. 18:315 (1970), Bayer, E. A. et al., Meth. Enzym. 62:308 (1979), Engval, E. et al., Immunol. 109:129 (1972), Goding, J. W., J. Immunol. Meth. 13:215 (1976).

In another example of the above methods, the antibodies are labeled such that a signal is produced when the two antibodies bind to the same molecule. One such system is described in U.S. Pat. No. 4,663,278.

In another embodiment of an antibody based detection system, a single antibody is employed which is capable of binding to an epitope which is present at the fusion junction of the NPM/ALK fusion protein but which is not present in the non-fusion NPM or ALK proteins. The fusion junction of the NPM/ALK fusion protein is described in FIG. 3b. A skilled artisan can readily employ the amino acid sequence of the fusion junction to generate peptide antigens for use in the above described methods of generating antibodies.

The materials used in the above assay methods (both nucleic acid and protein based) are ideally suited for the preparation of a kit. For example, for amplification based detection systems, the invention provides a compartmentalized kit to receive in close confinement, one or more containers which comprises:

(a) a first container comprising one or more of the amplification primers of the present invention; and (b) one or more other containers comprising one or more of the following: a sample reservoir, amplification reagents, wash reagents, and detection reagents.

For antibody based detection systems, the present invention provides a compartmentalized kit to receive in close confinement, one or more containers which comprises:

a) A first container comprising an antibody capable of binding to NPM;

b) A second container comprising an antibody capable of binding to ALK; and c) One or more other containers comprising one or more of the following: wash reagents and reagents capable of detecting the presence of bound antibodies from the first and the second containers.

The invention further provides a kit compartmentalized to received in close confinement one or more containers which comprises:

a) A first container comprising an antibody capable of binding to an epitope which is present in the fusion junction of the NPM/ALK fusion protein and which is not present in either of the two non-fusion proteins; and b) One or more other containers comprising one or more of the following: wash reagents and reagents capable of detecting the presence of bound antibodies from the first container.

In detail, a compartmentalized kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies or probes used in the assay, containers which contain wash reagents (such as phosphate buffered saline, Tris-buffers, etc.), and containers which contain the reagents used to detect the bound antibody or the hybridized probe.

For nucleic acid probes, examples of detection reagents include, but are not limited to radiolabeled probes, enzymatic labeled probes (horse radish peroxidase, alkaline phosphatase), and affinity labeled probes (biotin, avidin, or steptavidin). For antibodies, examples of detection reagents include, but are not limited to, labelled secondary antibodies, or in the alternative, if the primary antibody is labelled, the chromophoric, enzymatic, or antibody binding reagents which are capable of reacting with the labelled antibody. One skilled in the art will readily recognize that the antibodies and nucleic acid probes described in the present invention can readily be incorporated into one of the established kit formats which are well known in the art.

The present invention further includes methods for selectively killing cells expressing the NPM/ALK fusion protein. In detail, such a method comprises contacting a cell expressing the NPM/ALK fusion protein with a toxin derivatized antibody, wherein the antibody is capable of binding to the fusion protein but is incapable of binding to non-fusion NPM or ALK protein. Example of such antibodies are toxin derivatized antibodies which bind to fusion junction encoded by Seq. ID No. 2.

As used herein, an antibody is said to be "toxin-derivatized" when the antibody is covalently attached to a toxin moiety. Procedures for coupling such moieties to a molecule are well known in the art.

The binding of a toxin derivatized antibody to a cell brings the toxin moiety into close proximity to the cell and thereby promotes cell death. By providing such an antibody molecule to a mammal, the cell expressing the fusion protein can be preferentially killed.

Any suitable toxin moiety may be employed; however, it is preferable to employ toxins such as, for example, the ricin toxin, the cholera toxin, the diphtheria toxin, radioisotopic toxins, or membrane-channel-forming toxins.

The antibodies of the present invention may be administered to a mammal intravenously, intramuscularly, subcutaneously, enterally, topically or parenterally. When administering antibodies or peptides by injection, the administration may be by continuous injections, or by single or multiple injections.

The antibodies of the present invention are intended to be provided to recipient mammal in a "pharmaceutically acceptable form" in an amount sufficient to "therapeutically effective." An amount is said to be therapeutically effective if the dosage, route of administration, etc. of the agent are sufficient to preferentially kill a portion of the cells expressing the NPM/ALK fusion protein. An antibody is said to be "pharmacologically acceptable form" if its administration can be tolerated by a recipient patient. The antibodies of the present invention can be formulated according to known methods of preparing pharmaceutically useful compositions, whereby these materials, or their functional derivatives, are combined with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable composition which is suitable for effective administration, such compositions will contain an effective amount of an antibody of the present invention together with a suitable amount of carrier. In addition to carriers, the antibodies of the present invention may be supplied in humanized form.

Humanized antibodies may be produced, for example by replacing an immunogenic portion of an antibody with a corresponding, but non-immunogenic portion (i.e. chimetic antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., Science 240:1041–1043 (1988); Liu, A. Y. etal., Proc. Natl. Acad. Sci. USA 84:3439–3443 (1987); Liu, A. Y. et al., J. Immunol. 139:3521–3526 (1987); Sun, L. K. et al., Proc. Natl. Acad. Sci. USA 84:214–218 (1987); Nishimura, Y. et al., Canc. Res. 47:999–1005 (1987); Wood, C. R. et al., Nature 314:446–449 (1985)); Shaw et al., J. Natl. Cancer Inst. 80:1553–1559 (1988).

In providing a patient with a toxin derivatized antibody, the dosage of administered agent will vary depending upon such factors as the patient's age, weight, height, sex, general medical condition, previous medical history, etc. In general, it is desirable to provide the recipient with a dosage of the antibody which is in the range of from about 1 pg/kg to 10 mg/kg (body weight of patient), although a lower or higher dosage may be administered.

In another embodiment of the present invention, methods are provided for modulating the translation of RNA encoding the NPM/ALK fusion protein in the cell. Specifically, such method comprise introducing into a cell a DNA sequence which is capable of transcribing RNA which is complimentary to the mRNA encoding the NPM/ALK fusion protein. By introducing such a DNA sequence into a cell, antisense RNA will be produced which will hybridize and block the translation of the NPM/ALK fusion protein. Antisense cloning has been described elsewhere in more detail by Methis et al., Blood 82:1395–1401 (1993); Stein et al., Science 261:1004–1012 (1993); Mirabella et al., Anti-Cancer Drug Design 6:647–661 (1991); Rosenberg et al., Nature 313:703–706 (1985), Preiss et al., Nature 313:27–32 (1985), Melton, Proc. Natl. Acad. Sci. USA 82:144–148 (1985) and Kim et al., Cell 42:129–138 (1985).

Transcription of the introduced DNA will result in multiple copies of the antisense RNA being generated. By controlling the level of transcription of antisense RNA, and the tissue specificity of expression via promoter selection or gene targeting of the antisense expression sequence, one skilled in the art can regulate the level of translation of the NPM/ALK fusion protein in specific cells within a patient.

The level of expression of the NPM/ALK fusion protein can also be controlled through the use of ribozyme technology (for example, see Shore et al., Oncogen 8:3183–3188 (1993); Sarver et al., Science 247:1222–1225 (1990); and Cech, T., JAMA 260:3030–3034 (1988)). In detail, using known procedures, ribozymes specific for the NPM/ALK fusion mRNA can be generated and either supplied to or expressed within a cell. The supplying or expression of the ribozyme results in the cleavage of the mRNA encoding the NPM/ALK fusion.

In another embodiment of the present invention, methods are provided for identifying agents which are capable of binding to the NPM/ALK fusion protein herein described.

In detail, such methods comprise:
(a) contacting an agent with NPM/ALK fusion protein, or fragment thereof; and
(b) determining whether the agent binds to the fusion protein.

Using this method, agent which can be used to modulate the activity of the NPM/ALK fusion protein can be identified.

In another embodiment of the present invention, methods are provided for identifying agents which are capable of binding to the ALK protein herein described.

In detail, such methods comprise:
(a) contacting an agent with ALK protein, or a fragment thereof; and
(b) determining whether the agent binds to the ALK protein.

Using this method, agent which can be used to modulate the activity of the ALK protein can be identified. In addition, this method can be used to identify the ligand of the ALK protein.

There are numerous variations of the above assays which can be used by a skilled artisan without the need for undue experimentation in order to isolate agonists, antagonists, and ligands of ALK. For example an antibody can be used to co-precipitate the ALK bound agent to aid in purification and identification. In addition, the ALK protein, or a fragment containing the active site of ALK, can be used to screen an expression library for genes encoding proteins which bind ALK. Further, cells expressing ALK on their surface can be used as an alternative to using isolated ALK protein.

The agents screened in the above assay can be, but is not limited to, peptides, carbohydrates, or vitamin derivatives. The agents can be selected and screened at random or rationally selected or designed using protein modeling techniques. For random screening, agents such as peptides or carbohydrates are selected at random and are assayed for there ability to bind to the pseudogene peptide. Alternatively, agents may be rationally selected or designed. As used herein, an agent is said to be "rationally selected or designed" when the agent is chosen based on the configuration of the pseudogene peptide. For example, one skilled in the art can readily adapt currently available procedures to generate peptides capable of binding to a specific peptide sequence in order to generate rationally designed antipeptide peptides, for example see Hurby et al., Application of Synthetic Peptides: Antisense Peptides", In Synthetic Peptides, A User's Guide, W. H. Freeman, NY, pp. 289–307 (1992), and Kaspczak et al., Biochemistry 28:9230–8 (1989).

Using the above procedure, the present invention provides agents capable of binding to the NPM/ALK fusion protein, produced by the steps of:
(a) contacting said agent with NPM/ALK fusion protein, or a fragment thereof; and
(b) determining whether said agent binds to said NPM/ALK fusion protein.

Using the above procedure, the present invention provides agents capable of binding to the ALK protein, produced by the steps of:
(a) contacting said agent with the ALK protein, or a fragment thereof; and
(b) determining whether said agent binds to said ALK protein.

The present invention further provides methods of generating transgenic animals which contain the NPM/ALK gene fusion and/or the ALK gene. Such animals are useful as animal models for human t(2;5) lymphoma and for studying ALK function and activity.

In general, methods of generating transgenic animals are well known in the art (for example, see Grosveld et al., Transgenic Animals, Academic Press Ltd., San Diego, Calif. (1992)). Using the sequences disclosed herein for the NPM/ALK fusion or the ALK protein, a skilled artisan can readily generate a transgenic animal which contains and expresses the NPM/ALK fusion protein and or the ALK protein. Transgenic animals (such as mice and pigs) which express the NPM/ALK fusion can be used as an animal model for human t(2;5) lymphoma. Transgenic animals which express the ALK protein are useful for studying ALK function and activity. Such animals serve as models for the development of alternative therapies for t(2;5) lymphoma.

In addition to transgenic non-human mammals which have been altered to contain the human ALK gene or the NPM/ALK fusion gene, the present invention further provides non-human transgenic mammals which have been altered to "knock-out" the expression of the normal non-human mammalian homologue of the ALK gene. Specifically using procedures of gene targeting described elsewhere, a skilled artisan can employ the ALK gene of the present invention to inactivate (knock out) a homologous gene in a non-human mammal (Mansour et al., Nature 336:348–352 (1988)). The "knock out" prcedure has been successfully employed in a number or mammalian systems, for example see Lui et al., Cell 75:59–72 (1993). Because of the high degree of conservation of the ALK gene, the human Alk sequence can be employed in non-human mammals in the stanard knock out procedures.

Having now generally described in the invention, the agents and methods of obtaining same will be more readily understood through reference to the following examples which are provided by way of illustration, they are not intended to be limiting of the present invention unless specified.

EXAMPLE 1

To clone the genes altered by the t(2;5), we used a positional strategy based on fluorescence in situ hybridization (FISH) ordering of regionally derived cosmid clones. (In contrast to the majority of leukemia- and lymphoma-associated chromosomal translocations that have been molecularly characterized, the t(2;5) does not involve immunoglobulin or T-cell receptor genes, nor other cloned genes that have been previously localized to the breakpoint regions. Thus, to identify the breakpoint on chromosome 5, we isolated microdissection clones from bands 5q34–q35 and used them to identify 39 cosmid clones (D. Saltman et al., Nucleic Acids Res. 20:1401 (1992)), which then were oriented relative to the breakpoint by FISH analysis of metaphase chromosomes from the SUP-M2 and SU-DHL-1 t(2;5)-positive cell lines [R. Morgan et al., Blood 73:2155, (1989)]. Seventeen clones mapped centromeric and 22 clones telomeric to the breakpoint; clones from these groups were oriented relative to one another by two-color metaphase FISH analysis. FISH was performed as previously described [S. Morris et at., Blood 78:2013, (1991); D. Saltman et al., Genomics 16:726 (1993)]. The estimated genomic distance between the two cosmids that flanked the breakpoint most closely, designated cos47C12 (centromeric) and cos191E7 (telomeric), was 290 kb by interphase FISH analysis [J. Lawrence et al., Science 249:928 (1990); B. Trask et al., Am. J. Hum. Genet. 48:1 (1991)] in cells containing a normal chromosome 5. Despite their proximity to the chromosome 5 breakpoint, probes prepared from these cosmids did not detect rearranged restriction fragments by Southern blot analysis of pulsed-field gels prepared from DNA of t(2;5)-containing cell lines).

Figure 1A:
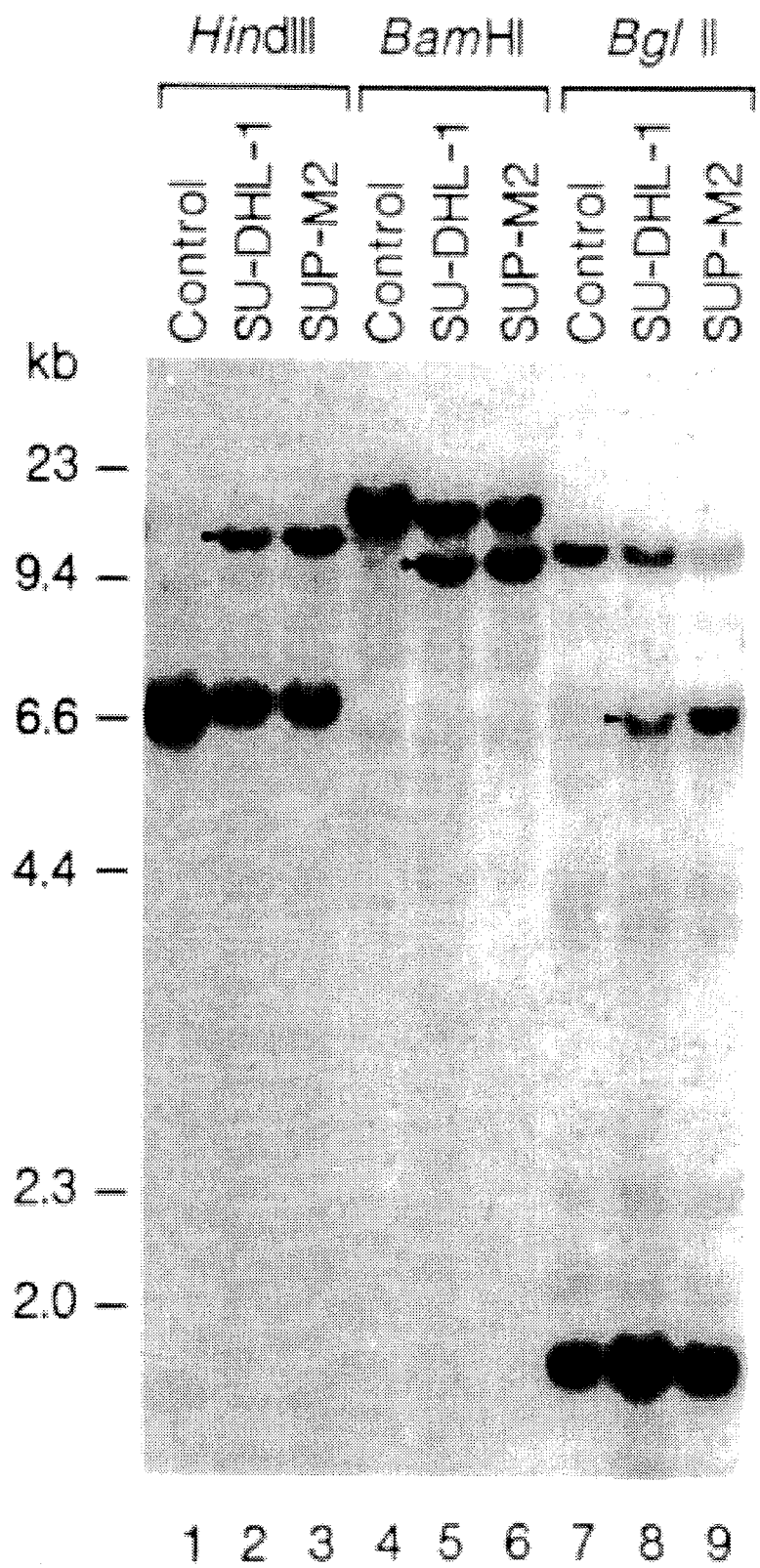
FIG. 1 (Panels A–C): (A) Southern blot analysis of DNAs prepared from a karyotypically normal, Epstein-Barr virus-immortalized human lymphocyte cell line (control, lanes 1, 4 and 7) and the t(2;5)-positive cell lines SU-DHL-1 (lanes 2, 5, and 8) and SUP-M2 (lanes 3, 6, and 9) with the p16-3/1.3S probe. Arrowheads indicate rearranged restriction fragments. (B) Northern blot analysis of RNAs from t(2;5)-negative B-lymphoid (NALM-6, lane 2), T-lymphoid (MOLT4, lane 1; CEM, lane 3) and rhabdomyosarcoma (Rh30, lane 7) transformed cell lines and the t(2;5)-positive lines SU-DHL-1, SUP-M2 and UCONN-L2 (lanes 4–6)

Bidirectional chromosome walks were performed from cosmids, approximately 290 kb apart, that flanked the breakpoint on chromosome 5; each walk spanned a genomic region of 150 kb. Using genomic probes isolated 70 kb from the telomeric cosmid, we detected rearranged restriction fragments in DNAs of two cell lines containing the t(2;5) (FIG. 1A) (Approximately 70 kb toward the breakpoint from the telomeric flanking clone, we isolated chromosome 5-specific genomic probes (p16-3/1.2S and p21-3/3E) that identified rearranged fragments with multiple enzymes in Southern blot analysis of DNAs from t(2;5)-positive cell lines. The genomic fragment p16-3/1.2S is located immediately centromeric to the chromosome 5 breakpoint, whereas p21-3/3E lies just telomeric to the break. Both probes identified a 1.6 kb transcript in Northern analysis of RNAs prepared from t(2;5)-positive and negative cell lines; in addition, p16-3/1.2S hybridized to a 2.4 kb transcript found only in t(2;5)-positive RNAs).

Figure 1B:
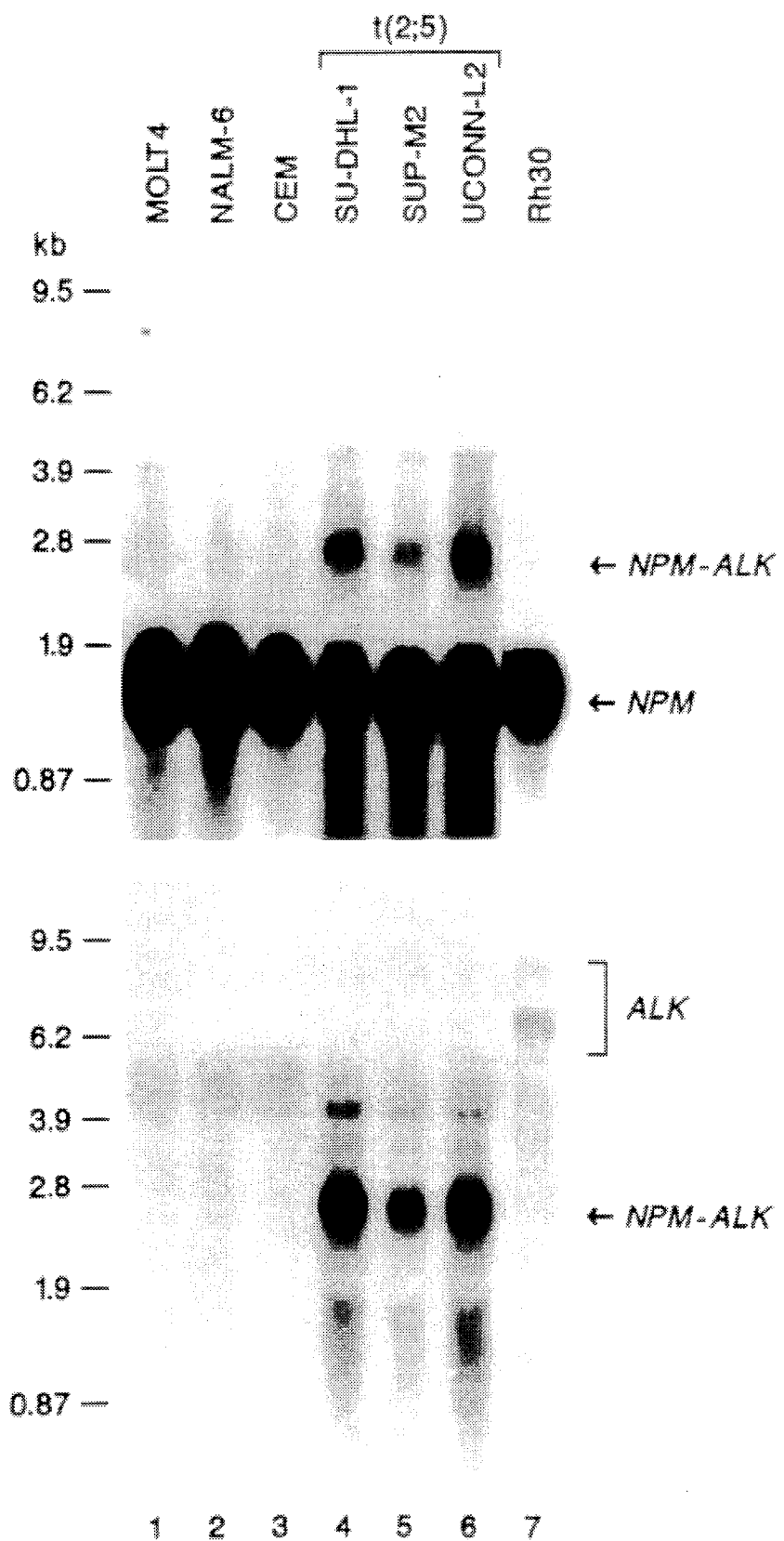

One of the probes (p21-3/3E) was hybridized to a cDNA library prepared from the polyadenylated RNA of the UOC-B1 pro-B leukemia cell line, which lacks the t(2;5). Multiple cDNA clones were isolated that hybridized to a ubiquitously expressed 1.6 kb mRNA, which was predicted by sequence analysis to encode nucleophosmin (NPM; also known as B23 or numatrin)—a highly conserved nucleolar phosphoprotein that shuttles ribosomal components between the nucleolus and the cytoplasm in the later stages of ribosome assembly (W. Y. Chan et al., Biochemistry 28:1033 (1989); R. A. Borer et al., Cell 56:379 (1989)). Probing of RNAs prepared from cell lines with or without the t(2;5), using a subclone from the 5' end of the NPM cDNA, identified both the normal NPM transcript and a 2.4 kb transcript restricted to t(2;5)-positive cell lines (FIG. 1B, top). A subclone containing 3' untranslated sequences detected only the normal 1.6 kb NPM transcript (not shown).

By screening a cDNA library prepared from the mRNA of the SU-DHL-1 t(2;5)-containing cell line, we isolated more than 20 clones that hybridized to 5' but not 3' NPM probes. Sequences from the 5' ends of the three longest clones were identical to 5' NPM cDNA sequences but diverged after the codon for Val$^{117}$. NPM sequences 3' of this codon were replaced by 1223 nucleotides, resulting in an open reading frame of 1575 nucleotides (FIG. 2A). A probe prepared from the 3' end of the fusion cDNA (pS1.2) identified the same 2.4 kb transcript that had been detected with the 5' NPM probe in RNAs from t(2;5)-positive cells (FIG. 1B, bottom). This fragment was localized to band p23 of chromosome 2 by hybridization to DNAs of human×rodent somatic cell hybrids and by metaphase FISH analysis (not shown), indicating that the 2.4 kb mRNA is encoded by a fused gene created by the t(2;5).

The 3' portion of the chimeric t(2;5) cDNA encodes conserved residues characteristic of the catalytic domain of members of the protein-tyrosine kinase (PTK) gene family (S. K. Hanks et al., Science 241:42 (1988); S. S. Taylor, et al., Annu. Rev. Cell Biol. 8:429 (1992)). (FIG. 2, A and C). Comparison of this newly identified anaplastic/ymphoma kinase (ALK) (NPM and ALK are approved HGM gene symbols. (P. McAlpine, personal communication)) with known PTK family members indicated greatest homology to members of the insulin receptor kinase subfamily, including leukocyte tyrosine kinase (LTK; 64% amino acid identity), TRKA (38%), ROS (37%) and its Drosophila homologue Sevenless (35%), the β-chain of the insulin-like growth factor-1 receptor (IGF1R; 37%) and the β-chain of the insulin receptor (IR; 36%) (J. J. Krolewski et al., EMBO J. 10:2911 (1991); H. Toyoshima et al., Proc. Natl. Acad. Sci. U.S.A. 90:5404 (1993); D. Martin-Zanca et al., Nature 319:743 (1986); H. Matsushime et al., Mol. Cell. Biol. 6:3000 (1986); J. M. Chen et al., Oncogene. 6:257 (1991); K. Basler et al., Cell 54:299 (1988); D. D. Bowtell et al., Genes and Development 2:620 (1988); A. Ullrich et al., EMBO J. 5:2503 (1986); A. Ullrich et al., Nature 313:756 (1985); Y. Ebina et al., Cell 40:747 (1985)).

The structure of normal ALK proteins was determined by screening a cDNA library prepared from a rhabdomyosarcoma cell line (Rh30), using the pS1.2 ALK probe. Analysis of the inserts of the two largest clones, pRMS4 and pRMS17-2, revealed 3' ALK sequences identical to those in the fusion gene cDNA, indicating that mutations had not occurred in the chimeric protein. Sequences of ALK immediately upstream of the NPM-ALK junction encoded 23 hydrophobic amino acids typical of a transmembrane domain (FIG. 2B), whereas those from the extreme 5' ends of the ALK clones were 50% identical to sequences encoding insulin-like growth factor binding protein-1 (IBP-1) (IBP-1 is a 30 kDa secreted protein found in human plasma and amniotic fluid that binds insulin-like growth factor-1 (IGF1) with high affinity [A. Brinkman et al., EMBO J. 7:2417 (1988); Y. L. Lee et al., Mol. Endocrinol. 2:404 (1988); M. Julkunen et al., FEBS Lat. 236:295 (1988)]). These comparisons indicate that the normal ALK product is a membrane-spanning tyrosine kinase receptor. Significantly, the transmembrane segment and putative extracellular ligand binding domain are not included in the NPM-ALK chimerio protein.

Figure 1C:
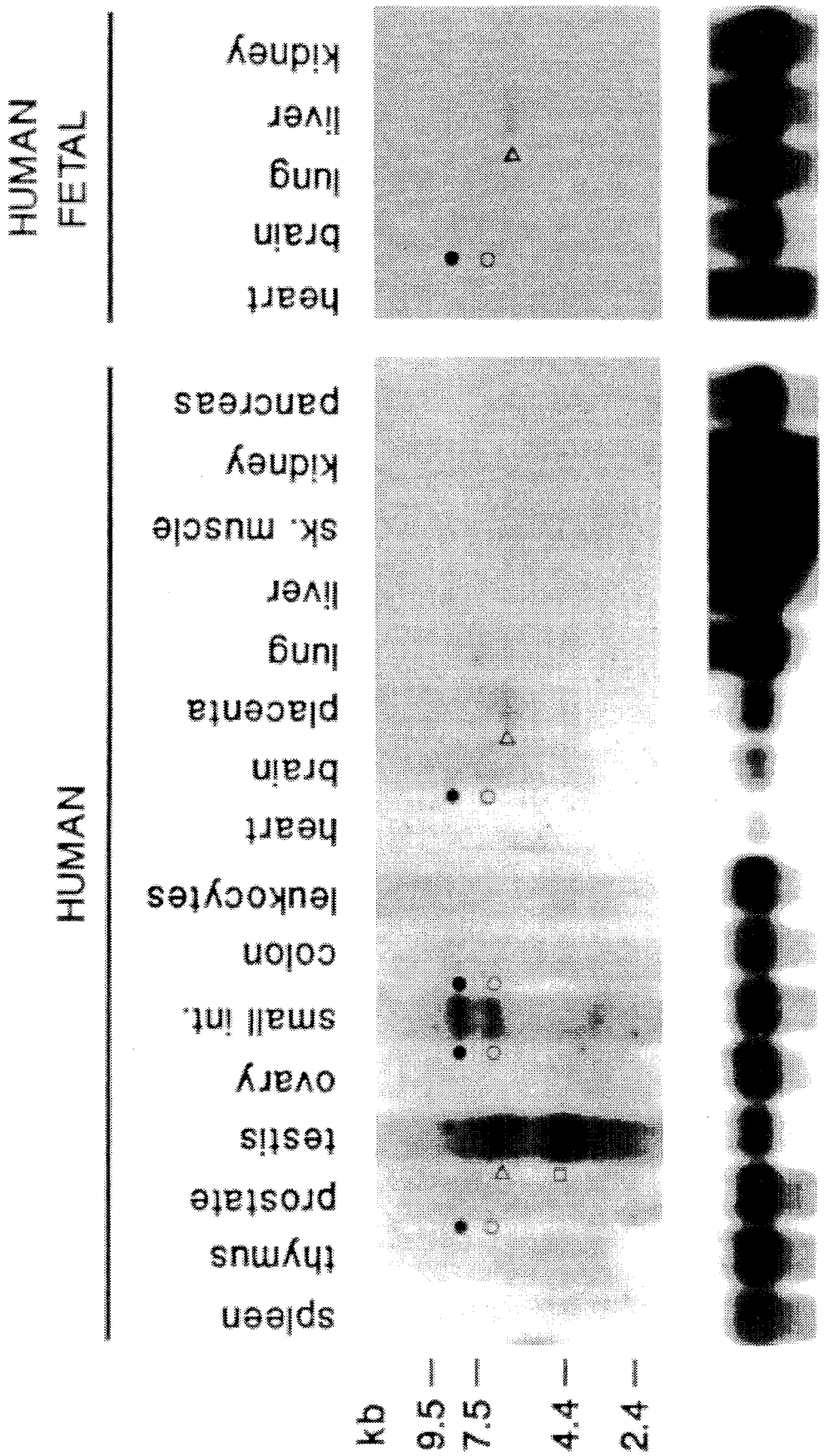

ALK mRNAs of 6.5 kb and 8.0 kb were readily identified in small intestine and rhabdomyosarcoma cell lines, and were weakly expressed in brain (fetal and adult), colon and prostate (FIG. 1, B [bottom] and C). Abundant amounts of 4.4 kb and 6.0 kb mRNAs were detected in testis, whereas placenta and fetal liver each expressed a single 6.0 kb transcript. All four mRNAs were also detected with a probe that contains only 3' untranslated ALK sequences, suggesting that they represent differentially spliced ALK mRNAs, not cross-hybridizing transcripts of other PTK genes. ALK transcripts were not detected in normal spleen, thymus, peripheral blood leukocytes, B-lymphoblastoid cell lines, phytohemagglutinin-stimulated T lymphocytes or t(2;5)-negative leukemia/lymphoma cell lines of myeloid or B- or T-lymphoid derivation, implying that they are not normally expressed in hematopoietic cells.

FISH mapping indicated that NPM and ALK are transcribed in centromeric to telomeric orientations on chromosomes 5 and 2, respectively, with the 2.4 kb fusion transcript arising from the derivative 5 translocated chromosome. Northern blot analysis provided no evidence for expression of a reciprocal ALK-NPM chimeric transcript, which could have been generated from the derivative 2 chromosome.

An RNA-based polymerase chain reaction (RNA-PCR) method confirmed the specificity of the fusion junctions in chimeric transcripts expressed in lymphomas harboring the t(2;5) (FIG. 3, A and B) (RNA-PCR was performed as previously described in E. Privitera et al., Blood 79:1781 (1992). Reactions were performed simultaneously with oligonucleotide primers specific for the chimeric NPM-ALK transcript (see FIG. 3B) and with a primer pair derived from the ubiquitously expressed NPM gene as a control for reverse transcription and amplification. A 3' NPM primer (5'-GCTACCACCTCC AGGGGCAGA-3' (Seq. ID No. 8)) was used with the NPM primer shown in FIG. 3B for the control amplifications; the 185 bp NPM product was detected by hybridization with an end-labeled oligonucleotide homologous to normal NPM sequences from the region in which the fusion junction occurs (5'-AGCACT-TAGTAGCTGTGGAGGAAG-3' (Seq. ID No. 9)). NPM-ALK fusion RNA-PCR products were detected with an end-labeled oligonucleotide that spans the fusion junction (5'-AGCACTTAGTAG TGTACCGCCGGA-3') (Seq. ID No. 10). Stringent post-hybridization washes were performed at 62° C. in 2×SSC/0.1% SDS for both the NPM-ALK and the NPM detection oligonucleotides).

Conversely, fusion transcripts were not detected in cell lines lacking the t(2;5), including several rhabdomyosarcoma lines that expressed ALK transcripts. NPM-ALK junction sequences were found in the RNAs of all seven t(2;5)-positive samples, including the SU-DHL-1, SUP-M2 and UCONN-L2 cell lines and diagnostic samples from four patients with anaplastic large cell lymphomas (The patient samples (three lymph node biopsies, one pleural effusion) were each shown by cytogenetic analysis to contain lymphoma cells bearing the t(2;5). The sequence of the RNA-PCR products from cells of patients 2 and 4 was determined and found to be identical to the cDNA sequence obtained from the SU-DHL-1 cell line (FIG. 3B). (Written informed consent was obtained from the patients or their parents, and investigations were approved by the clinical trials review committee of St. Jude Children's Research Hospital).

The breakpoints of the 2;5 translocation therefore appear to consistently involve the same introns of the NPM and ALK genes, leading to identical junctions in spliced mRNAs arising from the fused gene. Because of the difficulties in cytogenetic analysis of lymphoma biopsy samples, molecular detection of NPM-ALK fusion mRNAs by RNA-PCR should markedly improve the identification of these tumors.

The frequency of the t(2;5) in anaplastic large cell lymphomas indicates that the NPM-ALK product has a major role in the pathogenesis of these neoplasms. The normal NPM protein is a nonribosomal nucleolar phosphoprotein involved in the assembly of preribosomal particles into both small and large ribosomal subunits (W. Y. Chan et al., Biochemistry 28:1033 (1989); R. A. Borer et al., Cell 56:379 (1989); M. S. Schmidt-Zachmann et al., EMBO J. 6:1881 (1987); M. S. Schmidt-Zachmann et al., Chromosoma. 96:417 (1988); D. Hernandez-Verdun, J. Cell. Sci. 99:465 (1991)). It binds cooperatively with high affinity to single-stranded nucleic acids, exhibits RNA helix-destabilizing activity, and is found in association with the most mature nucleolar preribosomal ribonucleoproteins (T. S. Dumbar et al., Biochemistry 28:9495 (1989)). The relative abundance of NPM transcripts and protein is cell cycle regulated. NPM transcription and translation peak just prior to the entry of cells into S phase, with a decline to baseline just before the onset of G2 phase (N. Feuerstein et al., J. Immunol. 139:1818 (1987); N. Feuerstein et al., J. Biol. Chem. 262:11389 (1987); N. Feuerstein et al., J. Biol. Chem. 263:10608 (1988); N. Feuerstein et al., J. Cell Biol. 107:1629 (1988); N. Feuerstein et al., Exp. Cell Res. 194:289 (1991)).

Figure 3C:
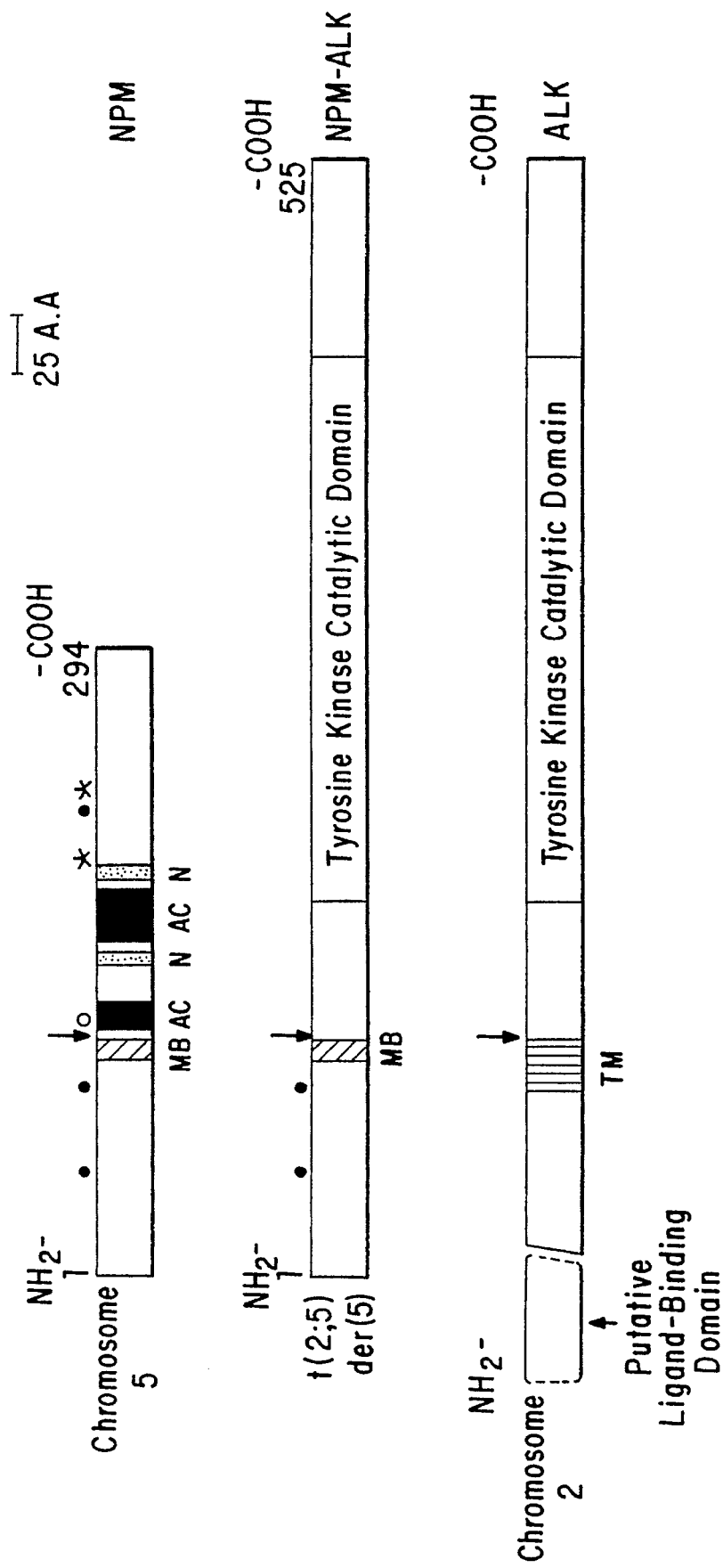

Sequences encoding most of the known structural domains of NPM are not incorporated into the fusion transcript (W. Y. Chan et al., Biochemistry 28:1033 (1989); R. A. Borer et al., Cell 56:379 (1989); M. Peter et al., Cell 60:791 (1990); P. K. Chan et al., Blochem. J. 270:549 (1990); R. Beckmann et al., Eur. J. Blochem. 210:45 (1992)) (FIG. 3C). We postulate that the NPM gene contributes an active promoter to drive expression of the ALK catalytic domain in lymphoma cells containing the t(2;5). This role for NPM would appear to be crucial, because the ALK promoter is normally silent in lymphoid cells. An oncogenic role, if any, for the amino-terminal NPM coding sequences incorporated into NPM-ALK, including those encoding potential protein kinase C phosphorylation sites (Ser[43] and Thr[78]) and a potential $C-X_5-H-X-_4H$ metal binding motif (residues 104–115), remains to be established.

The contribution of aberrantly activated receptor tyrosine kinases to malignant transformation is well recognized (J. Schlessinger et al., Neuron 9:383 (1992); T. Pawson, Curr. Opin. Gen. Dev. 2:4 (1992)). For example, malignant activation of TRKA can occur through gene fusions similar to NPM-ALK, in which the enzyme's extracellular domain is replaced by amino acids encoded by other genes, including those for nonmuscle tropomyosin and the ribosomal protein L7a (D. Martin-Zanca et al., Nature 319:743 (1986); F. Coulier et al., Mol. Cell. Biol. 9:15 (1989); R. Oskam et al., Proc. Natl. Acad. Sci. U.S.A. 85:2964 (1988); S. C. Kozma et al., EMBO J. 7:147 (1988); A. Ziemiecki et al., EMBO J. 9:191 (1990)). A consistent feature of oncogenic TRKA fusion proteins as well as other tyrosine kinase oncogenes, including BCR-ABL, EGFR, HER2/NEU and CSF-1R, is that much of their potency can be attributed to mutations or gene fusions that lead to a constitutively active catalytic domain (J. Schlessinger et al., Neuron 9:383 (1992); T. Pawson, Curr. Opin. Gen. Dev. 2:4 (1992); D. Martin-Zanca et al., Nature 319:743, (1986); F. Coulier et al., Mol. Cell. Biol. 9:15 (1989); R. Oskam et al., Proc. Natl. Acad. Sci. U.S.A. 85:2964 (1988); S. C. Kozma et al., EMBO J. 7:147 (1988); A. Ziemiecki, et al., EMBO J. 9:191 (1990)). Thus, in NPM-ALK fusion proteins, one would predict that the truncated ALK kinase is deregulated and phosphorylates intracellular substrates to trigger malignant transformation. Because anaplastic large cell lymphomas arise from activated T lymphocytes, which depend on IL-2 for growth and viability (K. A. Smith, Science 240:1169 (1988)), NPM-ALK may phosphorylate substrates that are normally phosphorylated in response to IL-2 receptor-mediated signals (E. M. Saltzman et al., J. Biol. Chem. 263:6956 (1988); D. K. Ferris et al., J. Immunol. 143:870 (1989); I. D. Horak et al., Proc. Natl. Acad. U.S.A. 88:1996 (1991); M. Hatakeyama et al., Science 252:1523, (1991); N. Kobayashi et al., Proc. Natl. Acad. Sci U.S.A 90:4201 (1993)), leading to constitutive activation of this signal transduction pathway.

Our findings stand in marked contrast to previous molecular genetic studies of T-cell lymphomas and leukemias arising in cells with an immature (thymic) immunophenotype. Chromosomal translocations in lymphoblastic T-cell malignancies consistently affect enhancers included in the TCR β-chain locus on chromosome 7, band q34, or the α/δ locus on chromosome 14, band q11 (M. L. Cleary, Cell 66:619 (1991); T. H. Rabbitts, Cell 67:641 (1991)). In each case, these enhancers, which are highly active in T-cell progenitors, cause dysregulated expression of developmentally regulated transcription factor genes (e.g., TAL/SCL, LYL1, RHOMB/TTG and HOX11) located at breakpoints on the reciprocal chromosomes. Our observations in large cell lymphoma suggest that the pathways leading to malignant transformation in mature T lymphocytes differ from those responsible for the differentiation arrest and altered growth of thymic progenitors.

What is claimed:

1. An isolated nucleic acid molecule having the nucleotide sequence of the human cDNA insert encoding anaplastic lymphoma kinase protein, ALK, contained in plasmid pRMS17-2, deposited at the American Type Culture Collection as ATCC designation 69497.

2. A vector construct comprising a vector into which has been inserted the isolated nucleic acid molecule of claim 1.

3. A cultured host cell transformed with the vector construct of claim 2.

4. The vector construct of claim 2, wherein said vector construct is plasmid pRMS17-2.

5. A host cell transformed with the vector construct of claim 4.

* * * * *